US006046002A

United States Patent [19]
Davis et al.

[11] Patent Number: 6,046,002
[45] Date of Patent: Apr. 4, 2000

[54] HIGHLY PARALLEL AND SENSITIVE METHOD FOR IDENTIFYING DRUGS AND DRUG TARGETS

[75] Inventors: Ron Davis; Guri N. Giaever, both of Palo Alto; Dan Shoemaker, Atherton, all of Calif.

[73] Assignee: The Board of Trustees of the Leland Stanford Junior University, Palo Alto, Calif.

[21] Appl. No.: 09/002,750

[22] Filed: Jan. 5, 1998

[51] Int. Cl.[7] ................................ C12Q 1/02; C12Q 1/68
[52] U.S. Cl. ................................ 435/6; 435/7.1; 435/7.2; 435/29; 435/91.2; 435/455; 435/325; 435/252.3; 435/254.11; 435/254.21; 435/254.2
[58] Field of Search ................................ 435/6, 7.1, 7.2, 435/29, 91.1, 91.2, 91.41, 91.5, 455, 325, 252.3, 254.11, 254.21, 254.2

[56] References Cited

U.S. PATENT DOCUMENTS

5,569,588  10/1996  Ashby et al. ................................ 436/6

OTHER PUBLICATIONS

DeRisi et al., "Use of a cDNA microarray to analyse gene expression patterns in human cancer" *Nat Genet* (Dec. 1996) 14(4):457–460.
Forozan et al., "Genome screening by comparative genomic hybridization" *Trends Genet* (Oct. 1997) 13(10):405–409.
Heller et al., "Discovery and analysis of inflammatory disease–related genes using cDNA microarrays" *Proc Natl Acad Sci USA* (Mar. 1997) 94(6):2150–2155.
DeRisi et al., "Exploring the metabolic and genetic control of gene expression on a genomic scale" *Science* (Oct. 1997) 278(5338):680–686.
Lashkari et al., "Yeast microarrays for genome wide parallel genetic and gene expression analysis" *Proc Natl Acad Sci USA* (Nov. 1997) 94(24):13057–13062.
Schuler et al., "A gene map of the human genome" *Science* (Oct. 1996) 274(5287):540–546.
Fraser et al., "The minimal gene complement of *Mycoplasma genitalium*" *Science* (Oct. 1995) 270(5235):397–403.

Fleischmann et al., "Whole–genome random sequencing and assembly of *Haemophilus influenzae* Rd" *Science* (Jul. 1995) 269(5223):496–512.
Schena et al., "Quantitative monitoring of gene expression patterns with a complementary DNA microarray" *Science* (Oct. 1995) 270(5235):467–470.
Schena et al., "Parallel human genome analysis: microarray–based expression monitoring of 1000 genes" *Proc Natl Acad Sci USA* (Oct. 1996) 93(20):10614–10619.
Shalon et al., "A DNA microarray system for analyzing complex DNA samples using two–color fluorescent probe hybridization" *Genome Res* (Jul. 1996) 6(7):639–645.
Shoemaker et al., "Quantitative phenotypic analysis of yeast deletion mutants using a highly parallel molecular barcoding strategy " *Nature Genetics* (Dec. 1996) 14:450–456.
Gossen et al., "Tight control of gene expression in mammalian cells by tetracycline–responsive promoters" *Proc Natl Acad Sci USA* (Jun. 1992) 89:5547–5551.
Palmer, "High throughput screening on a low budget" *Nature Biotechnology* (Apr. 1996) 14:513–516.
Liu et al., "Construction of a GAL1–Regulated Yeast cDNA Expression Library and Its Application to the Identification of Genes Whose Overexpression Causes Lethality in Yeast" *Genetics* (Nov. 1992) 132:665–673.
Rine et al., "Targeted selection of recombinant clones through gene dosage effects" *Proc Natl Acad Sci USA* (Nov. 1983) 80:6750–6754.
Rine, "Gene Overexpression in Studies of *Saccharomyces cerevisiae*" *Methods in Enzymology* (1991) 194;239–251.
Stewart et al., "Regulation of Gene Activity by Dosage Compensation at the Chromosomal Level in Drosophila" *Genetics* (Apr. 1975) 79:635–647.
Goffeau, et al., "Life with 6000 Genes," *Science* 274:546–567 (Oct. 25, 1996).

*Primary Examiner*—David Guzo
*Attorney, Agent, or Firm*—Carol L. Francis; Bozicevic, Field & Francis, LLP

[57] ABSTRACT

The invention features methods for identifying gene products that mediate a phenotype, such as drug resistance or sensitivity, as well as methods for identifying new bioactive compounds, by detecting differences in sensitivity of growth rate between host cells that differ in target gene product dosage (e.g., two copies of a target gene product-encoding sequence compared to one copy).

16 Claims, 8 Drawing Sheets

FIG. 1

1. Prepare a heterozygous deletion strain containing a deletion in a target gene and a molecular tag at the deletion site (1 functional copy of target gene). Wildtype organisms containing a molecular tag in a non-functional gene serve as the reference strain containing 2 copies.

t=0 hrs  All strains or equal abundance.

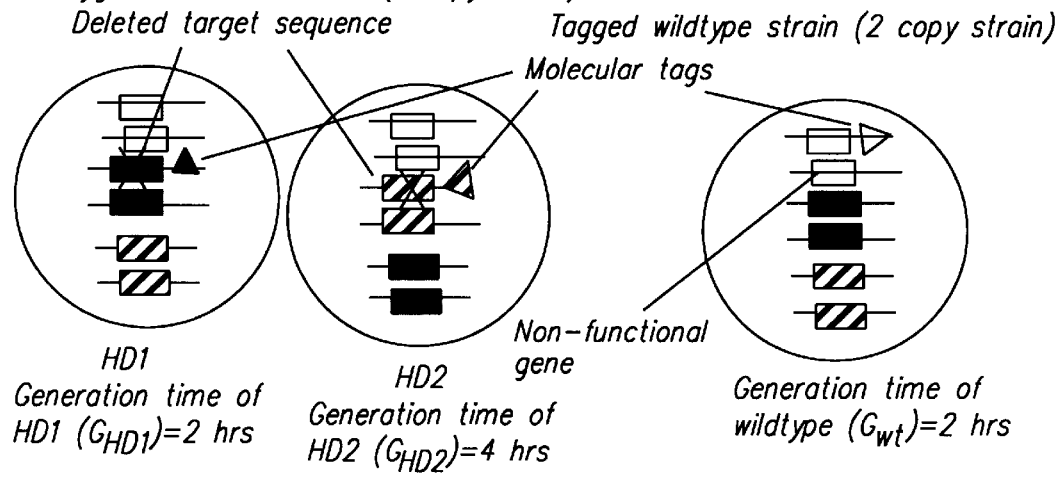

HD1
Generation time of
HD1 $(G_{HD1})$=2 hrs

HD2
Generation time of
HD2 $(G_{HD2})$=4 hrs

Generation time of
wildtype $(G_{wt})$=2 hrs

2. Grow heterozygote and wildtype strains in the presence of a known or candidate drug t=4 hrs HD1
generations = 2

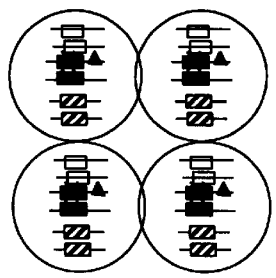

HD2
generations = 1

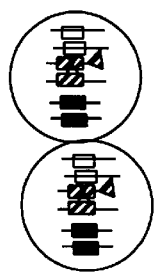

Wildtype
generations = 2

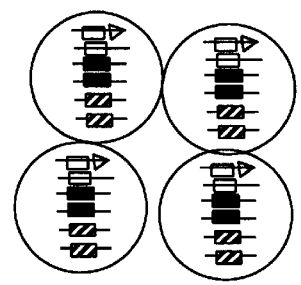

3. Analyze the population of cells within each sample. Compare the abundance of each of the strains by examining relative hybridization signals; this information can then be used to calculate growth rates of the strains. Identification of a heterozygous strain that becomes increasingly underrepresented with increasing culture time relative to diploid strain growth indicates that the heterozygote contains a deletion in a target gene that confers resistance to the drug.

Growth of alg7Δ/ ALG7 heterozygote and ALG7/ ALG7 wild-type (O.D.600) strains vs. time (hrs)

0μg/ml tunicamycin 0.5μg/ml tunicamycin

2μg/ml tunicamycin

—✳— alg7Δ/ALG7
—●— ALG7/ALG7

Growth of tub1Δ/ TUB1 heterozygote and TUB1/ TUB1 wild-type ($O.D._{600}$) strains vs. time (hrs)

0μg/ml benomyl

25μg/ml benomyl

50μg/ml benomyl

—✳— tub1Δ/TUB1
—●— TUB1/TUB1

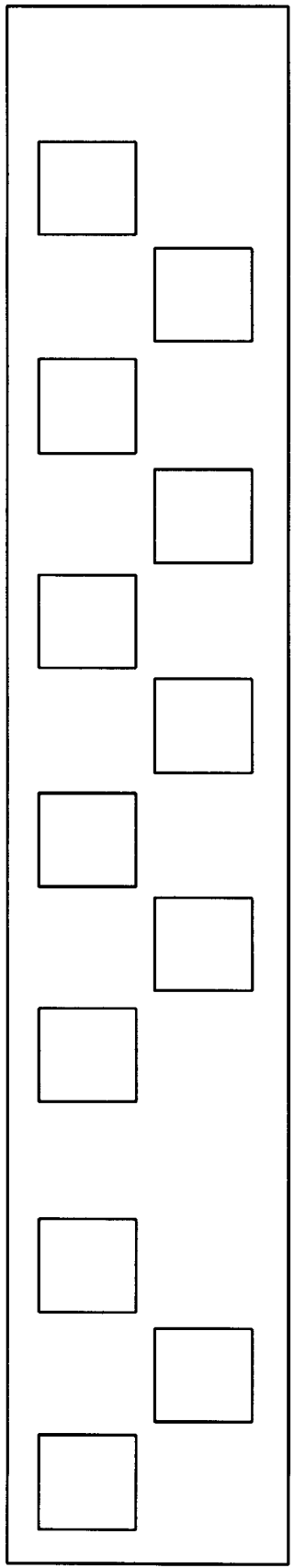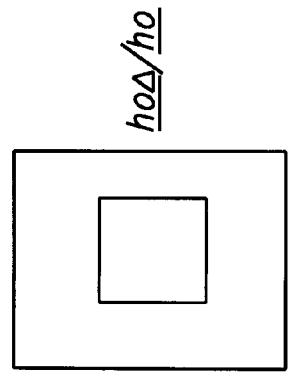
FIG. 11 strain/tag correlation on chip

HIGHLY PARALLEL AND SENSITIVE METHOD FOR IDENTIFYING DRUGS AND DRUG TARGETS

STATEMENT REGARDING GOVERNMENT SUPPORT

This invention was made with Government support under Contract No. HG 01663-01 awarded by the National Institutes of Health. The Government may have certain rights in this invention.

FIELD OF THE INVENTION

This invention relates to methods for the identification of gene products that mediate a phenotype, such as drug resistance or drug sensitivity.

INTRODUCTION

Traditionally the pharmaceutical industry has relied on two principal methods for drug discovery: 1) in vitro, cell-free biochemical assays; and 2) cell-based assays. In in vitro, cell-free biochemical assays, a massive library of compounds are screened against a given target. Biochemical assays identify compounds of interest by detecting the ability of the compound to alter activity of the target (e.g., by decreasing or increasing an enzymatic activity). The rapidity and efficiency of such screening methods have improved with the advent of automated techniques and advances in computer technology, thus facilitating discovery of important drugs (Palmer, 1996 *Nature Biotech.* 14:513–5).

However, the effectiveness of this high throughput approach to drug screening depends on the ability to design bioassays to test the activity of the target in the screen. The choice of target is then limited, in part, by the efficacy of designing a suitable bioassay amenable to automation. In addition, initial target selection is biased since investigators are often forced to select possible targets based only upon a combination of hearsay and empirical experience. Once a compound having a desired activity has been discovered using a biochemical in vitro cell-free assay, several caveats remain including whether the compound will interact with the target in vivo as it did in the cell-free in vitro assay, whether the compound will enter the cell to reach the target, and whether the compound will specifically affect the desired target without non-specifically affecting non-target gene products. In addition, this screening method makes it difficult to study natural broths or drug mixtures where drug concentrations may be too low.

In a second drug discovery method, the compounds are screened for a desired effect in a cell-based assay. Unlike in vitro biochemical assays, cell-based assays are based upon the ability of a compound(s) to affect some function or aspect of an entire organism and will identify compounds that have biologically significant effects. Conventional cell-based assays, however, also have limitations. For example, suitable in vivo assays must be designed, limiting the choice of targets. Cell-based assays can result in identification of compounds that non-specifically affect the cells. For example, investigators can use cell-based assays to identify compounds that generally affect cell growth, but since growth inhibitors may affect any of a variety of cell structures or enzymes, the investigators can not immediately and directly identify the specific target of the inhibitory compound. In these cases, the drug is either used without knowledge of the target or more likely is found to be of limited use due to nonspecific cytotoxic effects.

A direct approach for identification of drug targets is based on the notion that dramatically increasing dosage of the target gene (e.g., through the use of multicopy plasmids), and thus overexpressing the target gene product, will confer resistance to certain drugs. Thus, target gene products can be identified by constructing a library of cells, each cell carrying a multiple copy plasmid expressing a different candidate target gene, and growing the library in the presence of drug to select for those recombinant cells that, by virtue of increased dosage of the target gene, exhibit increased resistance to the drug. Evidence that overexpression of a gene can alter its sensitivity to a drug has been clearly demonstrated (see, e.g., Barnes et al. (1984) *Mol Cell. Biol.* 4:2381– 88; Rine et al. (1983) *Proc. Natl. Acad. Sci. USA* 80:6750–4; Rine (1991) *Meth. Enzymol.* 194:239–51).

Although gene overexpression using high copy number plasmids is a powerful technique for identifying gene products of interest, this approach has certain limitations. Gene product overexpression can itself be lethal to a host cell or can significantly alter the cell's usual biological pathways and processes (Liu et al. (1992) *Genetics* 132:665–73). Moreover, the copy number of the plasmid containing the gene of interest is not easily controlled or predictable (Rine, (1991), supra). Furthermore, growth under selective conditions, especially for long periods of time (e.g., days to weeks), encourages selection of mutant cells that may be altered in expression of gene products other than the gene product of interest. Thus, the target gene identified using this selection process does not always identify the true target of the drug.

Ideally, one would like a method to screen thousands of candidate drug targets simultaneously that would provide accurate and reliable information about the actual target(s) of the drug or candidate drug. The present invention addresses this problem.

RELEVANT LITERATURE

Targeted selection of recombinant yeast clones encoding drug resistance by dramatically increasing gene dosage is described in Rine et al. (1983) *Proc. Natl. Acad. Sci. USA* 80:6750; Rine (1991) *Methods Enzymol.* 194:239.

Analysis of yeast deletion mutants using a molecular bar-coding strategy is described in Shoemaker et al. (1996) *Nature Genet.* 14:450.

The complete sequence of the genome of *S. cerevisiae* is available at from http://sequence-www.stanford.edu/group/yeast_deletion _project/deletions3.html, and is discussed in Goffeau et al., (1996) *Science* 274:546.

SUMMARY OF THE INVENTION

The invention features methods for identifying gene products that mediate a phenotype, such as drug resistance or sensitivity, as well as methods for identifying new bioactive compounds, by detecting differences in growth (e.g, as measured by growth rate) between host cells that differ in target gene product dosage (e.g., two copies of a target gene product-encoding sequence compared to one copy).

Specifically, the invention features a method for identifying a nucleotide sequence encoding a target gene product of a bioactive compound by: a) culturing a first host cell and a second host cell in the presence of a bioactive compound, wherein the first host cell contains a target gene product-encoding sequence expressed at a first expression level, and the second host cell contains the target gene product-encoding sequence expressed at a second expression level, wherein the second expression level is less than the first expression level; and b) comparing growth rates of the first host cell and the second host cell. An alteration (e.g., increase or decrease) in growth rate of the second host cell relative to the growth rate of the first host cell indicates that the expression level of the candidate target gene product-encoding sequence is a determinant of resistance or sensitivity to the bioactive compound and the candidate target gene product-encoding sequence encodes a target gene product of the bioactive compound.

In still another aspect the inventions features a method for identifying a bioactive compound, the method comprising the steps of: a) culturing a first host cell and a second host cell in the presence of a candidate bioactive compound, wherein the first host cell contains a target gene product-encoding sequence expressed at a first expression level, and the second host cell contains the target gene product-encoding sequence expressed at a second expression level, wherein the second expression level is less than the first expression level; and b) comparing growth rate of the first host cell and the second host cell. An alteration (e.g., increase or decrease) in growth rate of the second host cell relative to the growth rate of the first host cell indicates that the candidate bioactive compound has activity toward the target gene product and that the expression level of the candidate target gene product-encoding sequence is a determinant of resistance or sensitivity to the compound.

In another aspect the invention features a method for identifying a nucleotide sequence encoding a target gene product of a bioactive compound by: a) culturing a reference host cell and a heterozygous deletion host cell in the presence of a bioactive compound, where the reference host cell contains two copies of a target gene product-encoding sequence, and the heterozygous deletion host cell contains i) a site-specific deletion of the target gene product-encoding sequence, and ii) one functional copy of the target gene product-encoding sequence; and b) comparing the growth rates of the reference host cell and the heterozygous deletion host cell. An alteration in growth rate (e.g., increase or decrease) of the heterozygous deletion host cell relative to growth rate of the reference host cell in the presence of the bioactive compound indicates that the heterozygous deletion strain contains a deletion in a target gene product-encoding sequence that encodes a target gene product of the bioactive compound.

In another aspect the invention features a method for identifying a bioactive compound by: a) culturing a reference host cell and a heterozygous deletion host cell in the presence of a candidate bioactive compound, where the reference host cell contains two copies of a target gene product-encoding sequence, and the heterozygous deletion host cell contains i) a site-specific deletion of the target gene product-encoding sequence, and ii) one functional copy of the target gene product-encoding sequence; and b) comparing growth rate of the reference host cell and the heterozygous deletion host cell. An alteration in growth rate of the heterozygous deletion host cell relative to the growth rate of the reference host cell indicates that the candidate bioactive compound has activity toward the target gene product deleted in the heterozygous deletion strain.

In a preferred embodiment, the host cells contain molecular tags that uniquely identify each host cell. For example, where target gene expression in the second host cell is less than target gene expression in the first host cell, the first host cell contains a first molecular tag uniquely associated with the first host cell and the second host cell contains a second molecular tag uniquely associated with the second host cell.

Likewise, where the method uses reference and heterozygous deletion cells, the reference host cell contains a first molecular tag (preferably inserted into a non-functional gene), and the heterozygous deletion cell contains a second molecular tag that is uniquely associated with the site-specific deletion of the heterozygous deletion host cell. Where arrays are used, comparison of growth rates of the host cells (e.g., by assaying samples as a function of time) can be accomplished by: a) amplifying (e.g., by PCR) the first and second molecular tags to produce first and second amplified tags, b) hybridizing the amplified tags to an array of oligonucleotides including sequences of the first and second molecular tags; and c) comparing hybridization signals of the first and second molecular tags. An difference in the hybridization signal of the second molecular tag relative to the hybridization signal of the first molecular tag is indicative of an alteration in growth rate of the host cell containing the second molecular tag relative to the first host cell in the presence of the compound.

In another preferred embodiment, the host cells are grown in a single culture. Preferably, the host cells are yeast strains.

In yet another embodiment, where the reference host cell is a wildtype host cell, and the growth rate of the wildtype host cell is compared to the growth rates of two or more heterozygous deletion host cells, wherein each of the heterozygous deletion host cells contains a deletion in a different target gene product-encoding sequence.

One advantage of the invention is that the strains having varying copy numbers of the target sequences (or which express the target gene product-encoding sequence at varying levels) are easy to make and collections can be custom designed to screen for drugs that inhibit specific cellular processes and targets.

Yet another advantage of the invention is that it does not require overexpression of the candidate target gene product sequence, which can itself decrease growth rate or be lethal. In contrast, a subtle change in copy number (e.g., a change of plus or minus one copy) minimizes physiological effect.

Another advantage of the invention is that the method is not dependent upon use of autonomous plasmids that are inherently unstable. Thus the problems associated with the effect of gross overexpression of a target sequence (e.g., expression of 10–50 copies) and/or the effects of bioactive compound on plasmid copy number and/or stability are avoided.

Still another advantage is that the invention can identify multiple targets of a drug.

The method of the invention is also advantageous in that it can be used with strains that are diploid ((2n); where "n" is the target sequence), heterozygous deletion strains (2n−1), haploid (n), or contain extra copies of the target sequence (e.g., (2n+1), (n+1), etc. where extra copies are preferably chromosomally integrated), and further allows for simultaneous screening of such strains.

Still another advantage is that the invention takes advantage of available genomic information. For example, if the complete or partial sequence of a potential target gene(s) is known, then one can readily construct strains for use in the invention, even if the function of the gene is unknown.

Another advantage of the invention is that information about the function of unknown genes can be readily attained in an in vivo system. For example, identifying strains that are sensitive or resistant to a known drug may reveal genes not otherwise known to be involved in the same pathway or parallel pathways.

Another advantage of the invention is that it facilitates the discovery of new drugs (e.g, antifungal, anti-cancer, etc.)

that affect the same target as known drugs, since once a heterozygous deletion strain is found to be sensitive to a known drug, this strain can then be used to find other drugs that affect the same strain.

The method of the invention is also advantageous in that it allows screening of many potential drug targets simultaneously (e.g., gene products involved in any cellular process such as DNA synthesis, assembly and function of the mitotic apparatus, sterol biosynthesis, cell wall biosynthesis, etc.), rather than testing such targets individually using conventional methods. For example, all possible targets can be tested using a collection of strains having deletions representative of the entire host cell's genome (e.g., using yeast as a host cell). Such a collection of yeast strains is presently under construction. Moreover, the invention allows for the identification of drug targets for known and new drugs alike, as well as the identification of new drugs that inhibit the same target as a known drug.

Another advantage is that, where the pathway or process inhibited by a drug is known, the method of the invention can be used to identify other drugs that affect this same pathway and that may have more specificity for a target in the pathway and/or fewer side effects than the known drug.

The method of the invention is also advantageous in that it is extremely sensitive, thus allowing detection of bioactive compounds at very low concentrations of the candidate compound. The invention thus allows discovery of drugs that would previously go undetected, and requires only a very small amount of candidate compound for screening.

Yet another advantage of the invention is that competitive growth assays are at least an order of magnitude more sensitive relative to other methods, such as methods that require measurement of colony forming units.

The invention is also advantageous in that it can facilitate identification of multiple drugs in a drug mixture or complex mixture of natural origin even if the drugs within the mixture have different targets. Furthermore, the methods allows identification of the targets.

The method of the invention is also advantageous in that it is readily adapted to high-throughput automation, is highly parallel and quantitative, and is rapid (i.e., assays can be carried out in a few hours). Moreover, because the assays do not require long term growth (e.g., more than 10–20 hrs, days, or weeks) the probability of selection for secondary mutations that might mask the effect of the true target gene is minimized.

Still another advantage of the invention is that it is relatively inexpensive to screen multiple drugs since, for example, collections of strains representing a large number of targets can be screened simultaneously in small culture volumes, and thus requires only a small amount of drug.

Another advantage of the invention is that once a target gene product(s) of a known drug is identified, the method can be used to identify other drugs that bind that same target gene product(s), thereby facilitating development of drugs that are both safe and effective, thus speeding the drug approval process.

Another advantage of the invention is that it can be readily adapted for use with a wide variety of host cells (e.g., haploid or diploid organisms; bacterial, yeast, or mammalian cells) and with a wide variety of candidate target gene product sequences.

BRIEF DESCRIPTION OF THE DRAWINGS

FIG. 1 is a schematic showing the general steps of the method of the invention.

FIG. 11 is a schematic of the oligonucleotide array which is labeled to provide a correlation of the position of each molecular tag on the array and the identity of the strain with which it is uniquely associated.

DESCRIPTION OF THE SPECIFIC EMBODIMENTS

Overview

Figure 2:
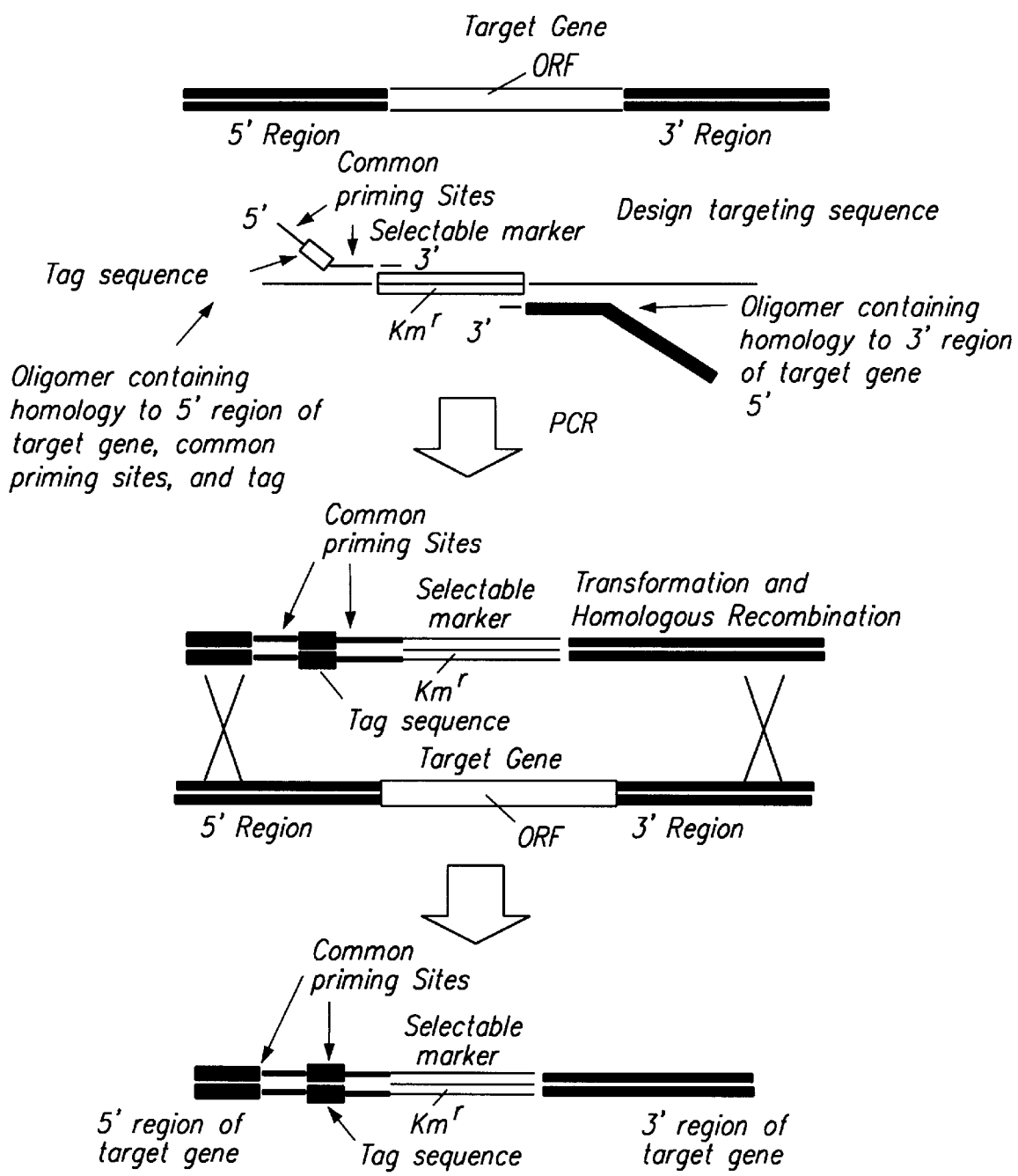
FIG. 2 is a schematic showing construction of a heterozygous deletion yeast strain using a single molecular tag.

The invention provides both 1) a means for identifying the target gene products with which a drug (i.e., a bioactive compound) interacts, and 2) a means for rapidly identifying compounds that elicit a measurable effect upon a target gene product of choice. Specifically, the method is based on the discovery that copy number of a gene encoding a drug target directly and sensitively determines the host cell's sensitivity to the drug to the degree that altering the target gene copy number from exactly 2 to exactly 1 elicits a detectable phenotypic change (e.g., a change in growth rate or fitness of the strain) in the presence of the drug. Although most heterozygotes reveal little or no phenotype under ordinary conditions, the present inventors have discovered that heterozygous deletion strains exhibit a phenotype when, for example, specifically stressed with a drug that inhibits the gene product that is heterozygous in that strain. Because altering copy number can be generally associated with alteration of gene expression levels (e.g., transcription, or translation), the method of the invention also encompasses the use of strains having altered expression levels of a target gene (e.g., by affecting the target gene's promoter).

FIG. 1 is a schematic showing the basic steps of the method of the invention. In this exemplary schematic, the host cells are a diploid cell and a heterozygous deletion strain. In general, a heterozygous deletion strain is prepared for each target gene of interest. As used herein, a "target gene" or "target sequence" is any genomic or episomal sequence encoding any open reading frame, i.e., a sequence encoding a polypeptide (normally of at least about 100 amino acids in length), peptide, oligopeptide, or functional RNA or DNA. Preferably, the deletion is associated with a unique molecular tag. The molecular tag is a nucleotide sequence unique to the deleted gene with which it is associated. The molecular tag can be amplified using a common set of primers and analyzed by its hybridization to a high-density oligonucleotide array containing the tag sequences (see, e.g., Shoemaker et al., 1996 *Nature Genetics* 14:450).

A strain containing a different number of copies of the target sequence relative to the heterozygous deletion strain (e.g., two or more copies) is also produced or identified as a reference strain. For example, as shown in FIG. 1, the reference strain can contain two copies of the target sequence. Such two copy strains can simply be a wildtype diploid strain, which is thus isogenic with the heterozygous deletion strain. Preferably, the wildtype strain contains a molecular tag in a non-functional gene or in a non-functional duplicated gene. The diploid strain's molecular tag allows for identification of the diploid strain when grown in the same culture with a heterozygous deletion strain(s). As a result, the two strains differ only in the copy number of a sequence encoding a potential or candidate target gene product and in the sequence of the molecular tag that identifies the strain as either a heterozygote (and further identifies the gene deleted in the heterozygote strain) or as a diploid strain.

analysis is the used to calculate growth rates of the strains in the pool (e.g., a heterozygous deletion strain with a decreased growth rate over time is associated with a decreasing hybridization signal of its corresponding tag). Each sample is analyzed to determine if, relative to any change in growth rate of the wildtype strain, a heterozygote strain becomes depleted from the culture with increasing culture time. Identification of such a heterozygote strain indicates that the heterozygote contains a deletion in a gene encoding a target gene product of the drug.

FIG. 1 illustrates the results of the method of the invention where, in the presence of a specific drug, the generation time of the heterozygous deletion strain HD1 (solid bar and triangle) is 2 hrs, the generation time of the reference strain (wildtype) is 2 hrs, and the generation time of the heterozygous deletion strain HD2 (striped bar and triangle) is 4 hrs (thus indicating that the HD2 strain carries a deletion in the drug's target). Thus, HD2 has a doubling time that is increased by two-fold relative to wildtype; in contrast, the HD1 strain has the same doubling time as the wildtype strain. Thus, while the strains are at roughly the same abundance at t=0 hrs, the difference in the growth rate of the HD2 strain relative to the reference wildtype strain will become readily apparent within only a few hours. For example, as shown in FIG. 1, the number of HD2 cells will be one-half the number of wildtype cells within the first 4 hrs of growth. The difference of the relative abundance of each strain as a function of time is illustrated in the Table 1 below.

TABLE 1

| Strain | # of generations* | | | # of cells | | | Abundance relative to wildtype** | | |
|---|---|---|---|---|---|---|---|---|---|
| Time | 0 hrs | 4 hrs | 20 hrs | 0 hrs | 4 hrs | 20 hrs | 0 hrs | 4 hrs | 20 hrs |
| Wildtype | 0 | 2 | 10 | 1 | 4 | 1024 | 1 | 1 | 1 |
| HD1 | 0 | 2 | 10 | 1 | 4 | 1024 | 1 | 1 | 1 |
| HD2 | 0 | 1 | 5 | 1 | 2 | 32 | 1 | 0.5 | 0.03 |

*The number of generations is calculated by dividing the growth time by the generation time.
**Abundance relative to wildtype equals the number of cells divided by the number of wildtype cells at a given timepoint.

As illustrated in FIG. 1, the invention can be used to identify a nucleotide sequence encoding a target gene product of an inhibitory drug by growing one or more heterozygote strains and a tagged reference strain, here exemplified as a wildtype strain, in the presence of the compound. Preferably, the strains are also grown in the absence of drug as a control. The method can involve growing one or more heterozygote strains, which can be grown either as individuals or in parallel by growth in the same culture as the diploid strains. Preferably, the heterozygote strains included in the culture contain deletions in a collection of genes representative of a set of genes of interest, such as the host cell's complete or partial genome, or a collection of genes encoding proteins representative of proteins important for a particular process or pathway, enzymes, structural proteins, or other possible targets.

The heterozygote and wildtype strains are grown in the presence of the drug for a period of time that allows for detection of a difference in growth rate between a heterozygote strain and the reference strain, usually on the order of about 10–24 hours. Generally, samples of the culture(s) are taken at different time intervals (e.g., every two hours). Tags are analyzed from each timepoint sample. The data from this The method of the invention can be readily adapted to simultaneously identify candidate drugs as inhibitory compounds and identify the target of the candidate drug's inhibitory action. In this embodiment, an alteration in growth rate of the heterozygous deletion strain relative to growth rate of the diploid strain indicates that the candidate drug has activity toward the target gene product (e.g., the drug interacts with the target gene product to elicit an effect on growth rate of the host cell) and that the heterozygous strain exhibiting decreased growth rate contains a deletion in a target gene product that confers resistance to the drug.

There are several possible outcomes to target sequence identification using the method of the invention. Some of the heterozygous deletion strains may be haploinsufficient in the absence of drugs (even when grown in rich medium), but still represent important drug targets. Because of their inherently slow growth rate, it may be desirable to study these strains in a separate pool to maximize the sensitivity of the method. Another interesting group of strains will be those that specifically respond to drugs. Such strains can be the result of at least two different mechanisms. First, the strain may carry a deletion of the gene that encodes a bona fide drug targets. The specificity of these strains to drug can then be verified through a number of different tests, drug-specific or target-specific tests, such as determining whether increasing copy number and/or overexpression of the putative drug target confers resistance to the drug. Alternatively, the strain may be sensitized as a result of deletion of a gene that is involved in a related pathway or process, but is not in the bona fide target gene per se. This group of strain is also interesting since such strain provide insight into, for example, possible sources of drug resistance.

The embodiment of the invention depicted in FIG. 1 can be readily applied to comparison of any two strains that express a target gene at differing levels, e.g., by virtue of different levels of transcription of the target gene in the two strains being compared. For example, a collection of strains having an inducible promoter operably linked to a chromosomal copy of a different target gene can be generated. The growth rates of these strains are compared under varying conditions of induction in the presence and absence of drug. The inducible promoter can provide for increased target gene product expression in the presence of inducer relative to expression in the absence of inducer (e.g., from about 1–1,000 times, preferably from about 1–10 times, more preferably from about 1–5 times uninduced target gene expression or more). Each inducible strain is associated with a unique tag that denotes the target gene for which expression is increased in the presence of inducer. The strains are then grown under the following conditions: 1) no inducer, no drug (lower target gene expresser); 2) with inducer, no drug (higher target gene expresser); 3) no inducer, with drug (lower target gene expresser); and 4) with inducer, with drug (higher target gene expresser). The collection of strains are grown in the presence and absence of a drug both with and without inducer. Drug targets are revealed where increased expression of a target protects the strain from the drug (or, by corollary, strains expressing the target gene at a lower level are depleted form the population in the presence of the drug). Strains that, in the presence of drug, exhibit decreased growth rate in the absence of inducer relative to growth rate in the presence of inducer contain a target gene that facilitates resistance to the drug.

The results of the method of the invention can be confirmed by constructing strains that contain increased copies of the target gene of interest. For example, the copy number of the target sequence of interest can be increased by introducing additional copies of the target sequence using recombinant DNA techniques (e.g., introduction of a recombinant construct containing the target sequence of interest resulting in episomal or chromosomal maintenance of the recombinant target sequence). If the sequence encodes a target gene product of the drug, then increasing copy number will lead to increased resistance of the host strain to the drug. Such results will strongly support the conclusion that the gene product is indeed a target of the drug.

Physiologically, the method of the invention does not perturb the cell significantly as judged by little or no alteration of growth rate or fitness, particularly when compared to methods that employ gross overexpression of the target gene product (e.g., methods that involve expression of greater than 5, 10, 50, 60, or even 80 copies of the target gene product-encoding sequence (see, e.g., Rine et al. (1983) *Proc. Natl. Acad. Sci USA* 80:6750)). Thus, in contrast to conventional methodology (e.g., Rine et al. supra), the method of the invention uses subtle changes in copy number and/or target gene expression to identify target sequences of interest.

Furthermore, while it is not surprising that large differences in copy number (or transcriptional levels) of the target sequence might result in appreciable differences in growth rate under test conditions (e.g., in the presence of drug), the discovery that small, incremental differences in copy number (or transcription levels) used in the method of the present invention resulted in marked growth rate differences was unexpected. No significant growth rate differences between most heterozygote and wildtype strains had been previously observed. Moreover, the conventional wisdom in the yeast genetics field suggested that, for most genes, no differences would be detectable upon comparing growth rates of heterozygotes and wildtype strains under test conditions, thus leading to the conclusion that the approach of the present invention would not be viable.

The present invention thus provides an elegant, genome-based, specific, parallel and sensitive method for drug discovery. The invention provides an efficient means for identifying the gene product, system, or pathway affected by a drug, such as an inhibitory agent or candidate drug and/or for identifying drugs having activity against a target gene product of interest or against one or more target gene products within a set of target gene products. In addition to drug discovery, the method of the invention has various applications in identification of the target/mechanism of candidate drug action, rational approaches to efficacy improvement, and rapid categorization of compounds as to possible therapeutic applications and potential toxicity. The method of the invention can also provide a means to identify genes that play a role in, or that can influence, a biological process or pathway or interest. Finally, the method of the invention is not limited by the available knowledge of the target genes or of the compounds to be screened. Rather, the claimed invention is useful in identification of targets of known drugs where the target is not known, simultaneous characterization of new drugs and their targets, and screening of a library of drugs (e.g., a mixture of drugs or compounds, natural extracts (including natural extracts that contain nonspecific toxins), or broths) to identify the affected targets.

Each step of the method will now be described in more detail.

Construction of Host Cells

Host Cells

The assay of the invention can be used in connection with any of a variety of host cells, including eukaryotic, prokaryotic, diploid, or haploid organisms, with the proviso that the host cell allows for genetic manipulation to provide for adequately precise regulation of target gene expression (e.g., the copy number of a target gene can be readily manipulated between two copies and one copy and/or the host cell allows for manipulation of transcription levels of a target gene to provided for altered expression levels). Host cells can also be either single cell organisms (e.g., bacteria, e.g., Mycobacterium spp., e.g., *M. tuberculosis*) or multicellular organisms (transgenic organisms, such as insects (e.g., Drosophila), worms (e.g., Caenorhabditis spp, e.g., *C. elegans*) and higher animals (e.g., transgenic mammals such as mice, rats, rabbits, hamsters, etc.). Preferably the host cell is a naturally diploid cell, preferably yeast cells (e.g., Saccharomyces spp. (e.g., *S. cerevisiae*), Candida spp. (e.g., *C. albicans*)) or mammalian cells. The host cell can also be a cell infected with a virus or phage that contains a target sequence in the viral or phage genome.

Yeast are currently a particularly preferred host cell for the method of the invention. Specifically, yeast naturally provides a powerful, easily genetically manipulatable model system which naturally contain target sequences of potential interest. For example, biochemical pathways exclusive to fungi can be enfeebled via gene disruption and potential drugs identified based on increased sensitivity to specific drugs compared with wildtype (Kirsch (1993) *Curr Opin Biotechnol* 4(5):543–552). Moreover, because of the extensive homology shared between yeast and human proteins (Foury, (1997) GENE 195:1–10), yeast can also be exploited to assay human drug targets by expressing a potential human drug target in the yeast host in lieu of the yeast homolog. Furthermore, identification of a target in yeast that shares homology with a human gene product can also provide information about the interaction the drug with the human homolog. Thus, the yeast provide a genetically manipulatable host cell, a genome encoding potentially interesting target sequences, and a system for expression of recombinant sequences from other organisms, especially human sequences. In general any method that results in target gene expression levels that provide for detectably different phenotypes (e.g., a detectable difference in growth rate) in the method of the invention can be used to generate strains for use in the claimed invention. Such methods include, but are not limited to, methods that alter the number of copies of the target gene (e.g., by decreasing target gene copy number (e.g., by deletion or otherwise rendering a target gene copy nonfunctional) or by increasing target gene copy number (e.g., by introducing an additional copy(ies) of the target gene), as well as methods that otherwise alter target gene expression levels in the host cell (e.g., by alteration of transcription levels (e.g., through use of a mutated native promoter or a heterologous promoter, including constitutive and inducible promoters), or by alteration of translation of target gene transcripts). Preferably, target gene expression is altered by altering copy number of the target gene.

Target Genes

The strains used in the invention can be altered in expression (e.g., by altering copy number or otherwise affecting transcription levels) of any gene of interest. It is not necessary that the function of the product encoded by the target gene be known; rather, the method of the invention can be used to determine whether the encoded unknown gene product plays a role in survival of the strain under a given set of conditions (e.g., presence of drug, increased temperature, nutrient-deficient medium, etc.). Thus, the target genes can encode any of a variety of gene products, including, but not limited to, genes encoding a protein having an enzymatic activity, structural genes (i.e., DNA sequences which encode a protein or peptide product), regulatory genes (i.e., DNA sequences which act as regulatory regions, such as promoters, enhancers, terminators, translational regulatory regions, etc., to affect the level or pattern of gene expression), and DNA sequences that encode a bioactive RNA, such as an antisense RNA (i.e., to provide for inhibition of expression of a host DNA sequence), or structural RNAs (i.e., RNAs with enzymatic activities or binding activities (ribozymes).

The method of the invention is not limited to examination of the role of "essential" genes, i.e., genes that are conventionally thought to be necessary for cell growth under a given condition or set of conditions. Rather, the invention recognizes that the concept of "essential" genes has hindered the discovery of genes with duplicative function or genes in duplicate pathways that can facilitate resistance to drugs that are targeted against "essential" genes. The exquisite sensitivity of the claimed method can be used to unmask such "nonessential" genes that encode potential drug targets of interest, thus facilitating the design of drugs that can be used alone or in combination with conventional drugs to minimize selection of resistant strains, reduce the amount of drug or the time of administration necessary to combat disease, and thus provide a means to avoid side effects associated with administration of high dosages or lengthy drug courses (e.g., toxicity to the subject and other side effects).

Constructing Host Cells Containing Different Copy Numbers of Candidate Target Gene Product-Encoding Sequences In one embodiment, the method of the invention employs strains having precise, varying copy numbers of the target sequence of interest. In any given strain, the copy number of the target sequence (i.e., the number of functional copies of the target sequence) is preferably either exactly two (i.e., diploid wildtype), exactly one (i.e., heterozygous deletion strain), or exactly three. A used herein "target sequence copy number" refers to the number of functional target sequences contained and expressed in a host cell. By "functional target sequence" is meant a nucleotide sequence that is expressed in the host cell to provide a functional gene product, i.e., a wildtype gene product that can serve its ordinary structural, enzymatic, or other function in the host cell.

The method of the invention can be used to analyze the effects of varying copy number of a single target sequence or to analyze simultaneously the effects of gene dosage of hundreds to thousands of different target sequences. For example, the cell population can comprise only one heterozygous deletion strain (and thus involve analysis of only one target sequence) or can comprise 10, 100, 500, 1,200, 6,200, or more heterozygous deletion strains (and thus the corresponding number of target sequences). The heterozygote strains used in the method can contain deletions in genes which collectively represent a set of gene of interest, such as the host cell's complete or partial genome. For example, where the host cell is yeast, the heterozygote strain collection can contain deletions in each of the approximately 6,000 genes of the yeast genome. Alternatively, the collection of heterozygotes can be tailored to screen a desired set of genes. For example, the heterozygote strain collection can contain deletions only in sequences encoding proteins for which a drug that specifically targets that gene product is desired (e.g., to find anticancer drugs that have the same target as benomyl using a tub1$\Delta$/TUB1 or a tub2$\Delta$/TUB2 strain).

Heterozygote Construction

Heterozygous deletion strains for use in the invention are constructed by site-specific deletion of a genomic sequence according to methods well known in the art. The site-specific deletion can be accomplished by using tagged transposons and retrospectively identifying strains containing the tagged transposons inserted into a desired gene. Alternatively, site-specific deletions can be generated using homologous recombination (e.g., Rothstein et al. 1991, supra). Where the host cell is a yeast cell, the heterozygotes are preferably constructed according to the methods of Rothstein (1991) *Meth. Enzymol.* 194:281–301, combined with the construction of strains containing molecular tags as per the method of Shoemaker et al. (1996) *Nature Genetics* 14:450, which involves incorporation of a molecular tag during the site-specific deletion process. The wildtype diploid host cell having a tag inserted in a non-functional gene can serve as the reference strain.

Of particular interest in the invention is the identification of strains that are haploinsufficient in the presence of drug, i.e., strains that display a growth rate phenotype in the presence of drug as a result of the presence of only one copy of the target gene. Identification of haploinsufficient strains indicates that even subtle change in gene dosage affect the fitness of the cell. Identification of haploinsufficient strains can have direct implications for drug therapy and the recommended therapeutic dosages and course. For example, identification of a drug that targets a gene product that is associated with haploinsufficiency in a heterozygous deletion strain suggests that the drug need only be administered in an amount that decreases the function of the gene product by about one-half; administration of an amount of drug sufficient to bind or inhibit function of all of the gene product may be unnecessary and even toxic, and may only serve to increase selective pressure for mutations in the target gene product.

In one embodiment, the method of the invention employs two complete genomic sets of genetically tailored yeast strains potentially sensitized or resistant to every possible drug target coded by the yeast genome. The first set is comprised of 6,000 heterozygote mutants (2n–1), with each strain carrying a deletion of a single genetic locus. In the second set, the gene dosage of every gene is systematically increased from one to two copies. This is accomplished by integrating a second copy of the target gene into the genome (2n+1). Production of such a collection of tagged heterozygous deletion strains is currently being carried out by a fifteen-lab international consortium. This collection of barcoded deletions will be available at http://sequence-www.stanford.edu/group/yeast_deletion _project deletions3.html.

The results of the method of the invention can be further confirmed, and the identified target further characterized, by producing host cells containing more than two copies of a target sequence. For example, strains containing three or more copies of the target sequence can be used to confirm results from analysis of strains containing one or two copies of the identified target sequence. Host cells containing more than two functional copies of a target sequence can be generated according to methods well known in the art. Preferably, such strains are generated by introducing the target sequence as a single copy in the chromosome (to produce a strain having a total of 3 copies of the target sequence) or on a multicopy plasmid such as CEN or a $2\mu$ circle (also known as Scp1), which provide for 5–10 copies and 60–80 copies of a target sequence, respectively (see, e.g., Rine et al. 1983 *Proc. Natl. Acad. Sci. USA* 80:6750–6754).

Construction of host cells having altered levels of expression of a target sequence by altering promoter activity The method of the invention encompasses identification of drug targets by altering expression of the sequence encoding the drug target. Alteration of target sequence copy number (e.g., from two copies to one copy) is only one means by which manipulation of target sequence expression can be achieved to facilitate identification of drugs targets according to the method of the invention. Alteration of target gene expression can also be accomplished by specifically altering the native promoter of the target gene. Alteration of target gene expression can also be achieved by construction of strains carrying a conditional mutation in a target gene, where the strain contains, for example, a temperature sensitive mutation in one copy of the target gene, which mutation renders the gene nonfunctional when grown at certain temperature. Alternatively, target gene expression can be altered by expression of antisense RNA to decrease expression of the target sequence. Thus, strains referred to herein as strains having "altered expression levels of a target gene" are thus meant to encompass strains having varying target gene copy number as well as strains containing other genetic alterations that provide for differences in transcription of a specific target sequence, e.g., by introduction of a heterologous promoter that facilitates transcription of the target gene in lieu of the native target gene promoter.

Alteration of transcription levels of the target gene can be accomplished by site-specific mutation of the native target gene promoter, or by replacement of the native promoter with a heterologous promoter. Methods for site-specific promoter alteration to affect alteration of transcription levels directed by the promoter (e.g., increase or decrease in transcription relative to the native promoter), as well as methods for introduction of heterologous promoters to drive transcription of a genomic sequence are well known in the art. Exemplary promoters include, but are not limited to, very weak constitutive promoters (e.g., yeast promoter KEX2), regulated promoters (e.g., the yeast promoters CYC1, PGK, and the yeast mating type-specific promoter MFα1), strong constitutive promoters (e.g., the yeast promoters TEF1, TDH), and inducible or repressible promoters (e.g., the yeast promoters GAL1, GAL7, GAL10, ADH1, ADH2, MT, PHO5), as well as promoters that provide for temperature-sensitive expression of the target gene. Methods for constructing strains having such heterologous promoters, and methods for inducing and/or maintaining a desired transcription level, and methods for qualitatively and/or quantitatively measuring transcriptional levels are well known in the art.

Exemplary promoters and such methods for their use are described in Nacken et al. 1996 *Gene* 175:253 (relative transcription levels of KEX2, CYC1, PGK, MFα1, TEF1, and TDH); Mylin et al. 1990 *Meth. Enzymol.* 185:297 (GAL1, GAL7, and GAL10; also describing use of the GAL expression system to obtain up to 60-fold increase in expression by using a strain containing both the chromosomal wildtype GAL4 gene and an expression cassette consisting of the GAL4 structural gene fused to the GAL10 promoter); Schneider et al. 1991 *Meth. Enzymol.* 194:373 (describing the GAL promoter system to provide regulated expression (e.g., using GAL1, which can provide 1000-fold induction in the presence of galactose and repression of expression in the presence of glucose), the ADHI promoter (which can provide 2-fold to 10-fold repression of expression in the presence of a nonfermentable carbon source), and the PGK promoter (which can provide for 20-fold to 30-fold repression of expression in the presence of a nonfermentable carbon source); Price et al. 1990 *Meth. Enzymol.* 185:308 (describing use of the ADH2 promoter to provide regulation of expression by glucose repression); Etcheverry 1990 *Meth. Enzymol.* 185:319 (describing use of the inducible MT promoter); Schena et al. 1991 *Meth. Enzymol.* 194:389 (describing use of the inducible strong promoter PHO5, the high-level constitutive yeast glyceraldehyde-3-phosphate dehydrogenase promoters (see also Schneider et al, supra), and glucocorticoid-inducible yeast expression vector p2UG in conjunction with the glucocorticoid receptor-encoding vector pG-N795). Additional promoters and expression systems are described in Emr 1990 *Meth. Enzymol.* 185:231; Rose et al. 1990 *Meth. Enzymol.* 185:234; Stearns et al. 1990 *Meth. Enzymol.* 185:280; Kingsmen et al. 1990 *Meth. Enzymol.* 185:329; Rosenberg et al. 1990 *Meth. Enzymol.* 185:341; and Sledziewski 1990 *Meth. Enzymol* 185:351. Also see generally Goeddel (ed.) 1990 *Expression in Yeast. Methods in Enzymology* 185 Section IV., Academic Press, San Diego, Calif.

Transcription levels can also be increased by introduction of additional copies of the target gene. This can be accomplished by, for example, introduction of an autonomous plasmid, which can be (and preferably is) chromosomally integrated into the genome of the host cell. Such autonomous plasmids are well known in the art and include, but are not limited to, 2-μm circle-based vectors (see, e.g., Rose et al., supra; Rose et al., supra), centromere-based (YCp) vectors, and ARS-based vectors (Rose et al., supra). For additional vectors useful in the invention, see Schena et al., supra (describing the pG-1, pG-2, pG-2, and p2UG/pG-N795 expression vector systems). The various promoters mentioned above can be used in conjunction with such plasmids to further increase expression levels of the target gene (see, e.g., Nacken et al., describing that a 3-log difference in expression levels of a gene can be obtained by varying promoter strength only, while introducing a single to high copy number plasmid can add an additional 100-fold increase in expression).

Preferably, the method of the invention uses strains that differ subtly in expression of the target gene, e.g., by at least about half-fold, by at least about 2-fold (e.g., a two copy strain compared to a one copy strain), by at least about 3-fold, by at least about 4-fold, and up to about 5-fold to about 10-fold or more. In general, expression levels of the target gene can be altered from about 0.5-fold to about 1,000-fold, and can be from about 0.1-fold to 10,000-fold. Preferably the expression levels differ by less than about 10-fold and may be less than about 5-fold. The method of the invention can also be used in conjunction with strains that differ in expression of the target gene by greater degrees (e.g., by about 100-fold to about 1,000-fold) providing that the target gene expression allows for detection in growth rate differences between the strain grown in the presence and absence of drug relative to the growth rate of a strain having a differing level of expression (e.g., relative to wildtype) in the presence and absence of drug.

The method of the invention can also be used in conjunction with host cells containing multiple mutations. For example, the strain can contain a "double knock-out," i.e., the strain is deleted for two different genes, and thus is a "double heterozygote deletion strain." Since some mutations may only demonstrate an effect in the context of a second mutation, the use of strains containing multiple mutations may reveal additional targets.

Molecular Bar-Coding

Preferably, the strains used in the method of the invention are designed to contain a molecular tag. A "molecular tag," also known as a molecular bar code, is a nucleotide sequence, usually of about 20 nucleotides in length, which is unique to the altered gene with which it is associated. The molecular tags are preferably designed so that all tags in a host cell culture of the invention can be amplified with a single set of common primers (see, e.g., Shoemaker et al., 1996 *Nature Genetics* 14:450) and quantitatively identified by hybridization. This embodiment thus facilitates analysis of a large number of strains, each of which contains a deletion or other target gene alteration associated with a unique tag, in a highly parallel fashion. Moreover, use of molecular tags allows pooling of strains having differing target gene expression levels (e.g., pooling of heterozygote and diploid strains). Methods for preparation of molecular tags (Shoemaker et al., 1996 *Nature Genetics* 14:450) and production of strains (Rothstein (1991) *Meth. Enzymol.* 194:281) containing such tags are well known in the art.

FIG. 2 illustrates an exemplary method of generating tagged heterozygous deletion strains. Briefly, a selectable marker, such as a kanamycin resistance gene, is amplified using a pair of long primers (e.g., 86mer and 68mer). The first primer contains a targeting sequence that has homology to the 5' end of the target genomic sequence to be deleted, while the second primer contains a targeting sequence having homology to the 3' end of the target sequence. One of either the first or second primers is also designed to contain a molecular tag (e.g., a 20 bp unique nucleotide sequence) as well as common tag priming sites flanking the molecular tag sequence. The common tag priming sites, which are generally about 18 bp in length, are common to all molecular tags used in any one set of strains to be used in the method of the invention. Thus the common tag priming sites of all heterozygote and diploid strains in a set of strains can be amplified using a single set of primer sequences that are homologous to the common tag priming sites.

The heterozygous deletion strains can be constructed by introducing the amplified selectable marker into the host cell's genome in a site-specific manner, thus rendering one of the target sequences non-functional. Where the host cell is a yeast strain, the amplified selectable marker containing the molecular tag can be transformed into a haploid yeast strain, the marker integrated into the target sequence by homologous recombination, and the resulting haploid deletion strain mated to produce a diploid strain that is heterozygous for the target sequence. More simply, the amplified selectable marker can be transformed into a diploid yeast strain to directly produce a heterozygous deletion strain (e.g., for essential genes). In contrast to the method for generation of haploid deletion strains described in Shoemaker et al., supra, it is of great importance to the present invention that the final heterozygous deletion strain contain one non-functional copy of the target sequence (due to insertion of the selectable marker) and one functional copy of the target sequence, but is otherwise diploid for all other non-target sequences.

Figure 3:
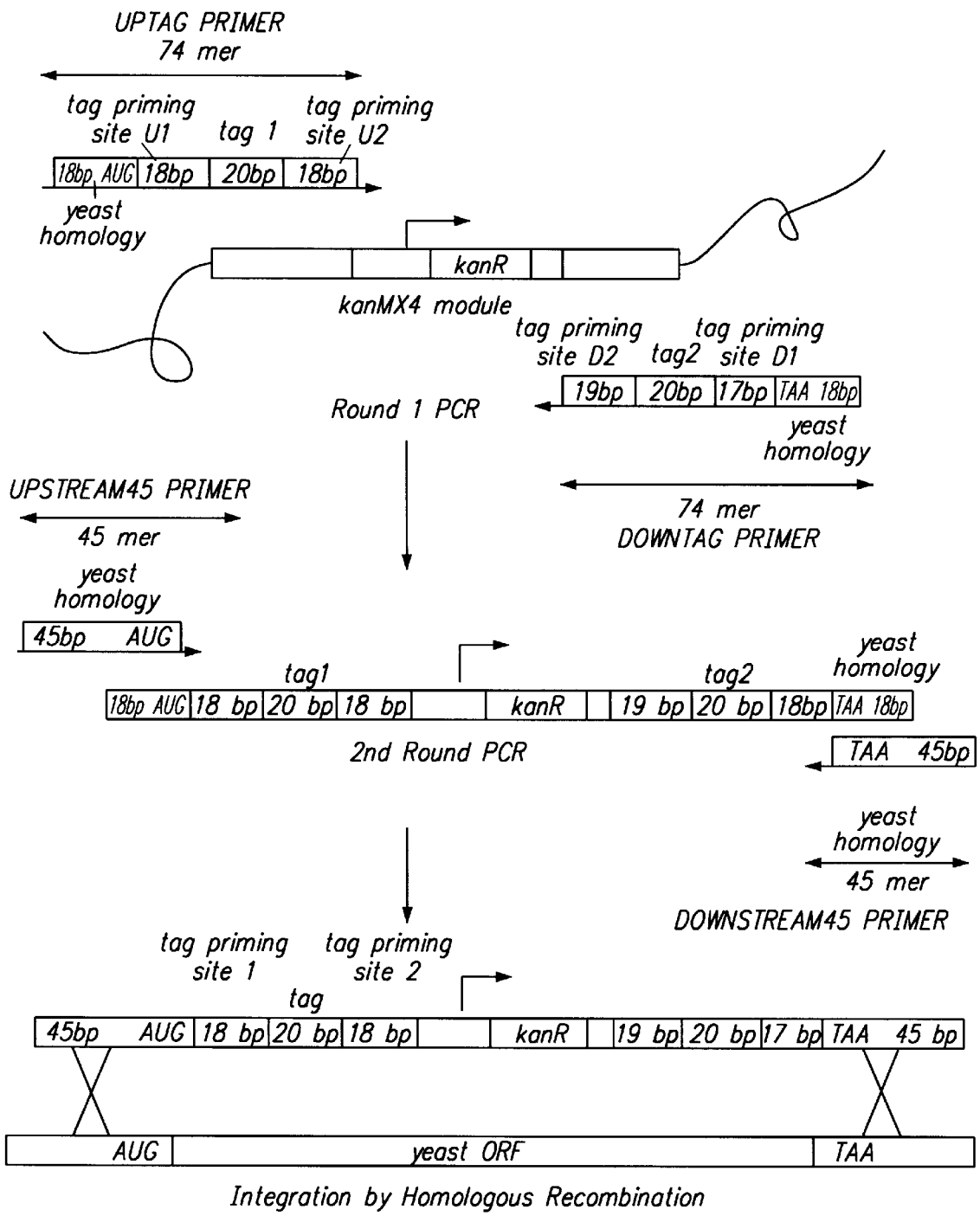
FIG. 3 is a schematic showing an exemplary scheme for generating strains containing two molecular tags.

In an especially preferred embodiment, the strains used in the invention contain two tags for each gene to be analyzed. An exemplary scheme for generating stains having two tags is shown in FIG. 3. Construction of strains containing two tags is similar to that described above for construction of strains containing a single tag, with the exception that both the primer containing homology to the 5' sequence of the target gene and the primer containing homology to the 3' region of the target gene contain tag priming sties and tag sequences. Use of two tags increases the sensitivity and multiplies the probability of identifying a strain correctly. Moreover, use of two tags decreases the incidence of errors or other problems in strain identification due to errors associated with tag synthesis or mutation of tag sequences during growth. Given the description of these two tagging strategies, it will be apparent to one of ordinary skill in the art that these strategies can be modified to construct strains having any number of tags, as well as construction of strains having tags that render one or more target sequences which a tag is associated non-functional.

Tagged diploid strains can be constructed in a manner similar to the construction of the haploid strains, except that the target sequence is a non-functional sequence, i.e., a sequence that does not substantially affect the diploid strain's growth rate or fitness under any growth conditions that may be used in the method of the invention. Examples of such non-functional genes include genes that are non-functional and duplicated, that have been altered to render the gene non-functional, but yet does not affect the strain's growth rate, and/or pseudogenes. For example, where the host cell is a yeast strain, the non-functional sequence that is tagged in the diploid strain is a non-functional HO gene, which when functional facilitates switching of mating types. Non-functional sequences suitable for tag insertion can be identified by making strains having tags in different is 5 candidate non-functional genes and testing such strains to determine the insertion of the tag has a detectable affect on growth rate of the strain. Tagged control strains, such as the tagged diploid strain described above, can contain two or more tags in the same or different non-functional gene(s).

Tagged strains having altered expression of a target sequence due to the presence of a heterologous promoter (e.g., an inducible promoter or a promoter having a promoter strength different from the native target gene promoter) can be constructed in a manner similar to that described above (e.g., by introduction of the molecular tag sequence concomitant with replacement of the native promoter). It is not necessary that the molecular tag be at or near the site of the genomic alteration (e.g., the site of the site-specific deletion or at the site of promoter alteration). Rather, it is only necessary that the molecular tag be present within the same cell, preferably on a stable episomal element or in the genome, in a manner that does not affect any functional genes in the strain (i.e., does not affect strain growth or fitness) and uniquely identifies the strain (e.g., the molecular tag identifies the strain as the strain that contains the particular site-specific deletion, or the particular promoter alteration).

Test Growth Conditions for Comparison Growth Rate/Fitness

The strains having differing levels of target gene expression (e.g., a diploid (two copy) and a heterozygous deletion (one copy) strain) can be grown under any of a variety of conditions to identify gene products that are important for growth under the given condition. For example, the method of the invention can be used to identify gene products important in growth of host cells under temperature extremes (e.g., high or low temperature), varying ionic conditions (e.g., high concentrations of salt), or pH extremes (e.g., acid or basic culture conditions). Of particular interest is the identification of gene products important in the growth of strains in the presence of a bioactive compound (i.e., drug) or in the presence of a candidate bioactive compound (i.e., candidate drug). Preferably strains are also grown in the absence of drug as a control. Strains can be grown in either liquid or on solid medium, preferably liquid medium. Where the strains are grown in liquid culture, the strains can be grown in small volumes (e.g., a volume of about 100 µl, about 200 µl, about 300 µl, about 500 µl, about 1 ml, or about 5 ml).

Differences in growth rate can be assessed by any of a variety of means well known in the art. For example, growth rate can be determined by measuring optical density (OD) as a function of time according to methods well known in the art. Preferably differences growth rate are detected using the molecular bar coding and microarray strategies described herein. In general, as used herein, "growth rate" means the generation time or doubling time of the host cell. Thus an increase in growth rate is associated with an decrease in generation time or doubling time, while a decrease in growth rate is associated with an increase in generation time or doubling time. Growth rate differences as small as about 5% and even less than or about 1% can be detected using the method of the invention. In general, the strains being analyzed are grown competitively in a single pool, where the starting pool is composed of strains at equal abundance. Where molecular tags and microarrays are used to assess growth rate, growth rate differences in the strains are detected by detection of a depletion of the strain's tag hybridization signal over time.

Bioactive compounds for analysis

"Bioactive compounds" and "drugs" are used interchangeably herein to denote any chemical compound or agent, e.g., a synthetic compound or compound isolated from natural sources, that alters a biological process in a manner that is detectable using the method of the invention. Bioactive compounds suitable for analysis are normally initially identified as modifiers of a process, whereby their modifying effect can provide the basis for an in vivo selection. For example, in the simplest case, the modifying effect would be cell death, or severe growth rate inhibition. A "candidate bioactive compound" or "candidate drug" is a natural or synthetic compound that may have the characteristics of a drug in the alteration of a biological process either by interaction with the same target or a different target.

The method of the invention can be used to identify the gene product targets of any bioactive compound (or candidate bioactive compound) that has a modifying effect that can provide the basis for an in vivo selection. Bioactive compounds (or candidate bioactive compounds) suitable for analysis using the claimed method include, but are not limited to, antibiotics (e.g., antibacterial, bacteriostatic, and antifungal agents), chemotherapeutic agents, agents that affect (inhibit or enhance) a biosynthetic pathway, and the like.

According to the method of the invention, the modifying effect of the bioactive compound examined is growth inhibition of a host cell, which can be manifested as, for example, a lag in doubling time of a culture, and can be as severe cell death after culturing the host cell in the presence of the agent.

Growth Conditions

The test growth condition can be any condition that allows for detection of a difference in growth of strains expressing the target gene sequence at differing levels (e.g., a difference in growth of diploid and heterozygous deletion strains). Test growth conditions can include, but are not limited to, growth in minimal media, growth under a given temperature or temperature range, or growth in the presence of a bioactive compound or candidate bioactive compound, e.g., an inhibitory compound. Preferably, a control cell culture is grown in parallel under control growth conditions that are amenable to normal host cell growth (e.g., in the absence of drug or in complete medium). Where the growth condition involves the presence of an inhibitory drug (or a candidate drug), the drug is present in the culture at a concentration sufficient to allow detection of a difference in growth rates between the strains being tested (e.g., between a two copy (diploid) strain and a one copy (e.g. heterozygote deletion) strain). Where the host cells are yeast, the growth conditions are normally in YPD medium at 30° C. either with or without drug.

The strains are grown under the growth conditions (e.g., in the presence and absence of drug) for a period sufficient to detect any difference in growth rates of the strains. In general, such growth rate differences can be detected after about 2 hours growth or less, usually at about 2 to 4 hours growth, generally within about 4 to 6 hours growth, normally within about 6 to 8 hours growth, and normally do not require more than about 10 hrs to about 12 hours growth for detection. In general, growth rate differences can be detected in less than 12 hours of growth. Stated differently, growth rate differences can be detected in about 2 generations to 4 generations, usually in about 3 generations to about 4 generations, more usually in about 4 generations to about 5 generations, and can be observed in about 8 to 10 generations, usually within or less than 10 generations. Thus, because the assays do not require long term growth (e.g., the assay does not require long-term growth of more than 24 hours or even a week as in conventional assays), the present invention minimizes the likelihood of selection of strains containing secondary mutations.

The method of the invention can be made even more sensitive to slight differences in expression of a target gene by globally decreasing transcription of all genes, e.g., by use of actinomycin in the cultures. The effects of target gene expression upon growth rate can also be examined under differing growth conditions, e.g., in media of differing nutrient composition (e.g., to simulate differing in vivo environments), as well as differing temperatures (e.g., to simulate the body temperature of the subject that may receive therapy using the identified drug or drug being tested).

Identification of Target Gene Product-Encoding Sequences and/or Bioactive Compounds After growth under a test condition as described above, the effect upon strain growth rate is analyzed. Where the strains are designed to contain a molecular tag, the relative abundance of each of the tagged strains can be determined by amplifying the tags using conventional PCR methods and the appropriate common primers. The amplified tags are then analyzed to compare, either quantitatively or qualitatively, the relative amounts of, for example, each heterozygote tag and diploid tag in a sample. The relative amounts of the tags are correlated to the relative abundance of the strains in the sample.

Analysis of the amplified tags can be accomplished according to any of a variety of methods well known in the art that allows for differentiation of the tag sequences. For example, where the tag sequences are of sufficiently different lengths, the tag composition in a sample of amplified tags can be analyzed using Southern hybridization techniques, or by hybridization to filters having bound sequences complementary to the tags.

Molecular Tag Analysis Using an Oligonucleotide Array

Preferably, the composition of the amplified tag sequences is analyzed by hybridizing the amplified tags to a high-density oligonucleotide array containing all tag sequences in the population (see Shoemaker et al. (1996) *Nature Genet.* 14:450). Methods for making oligonucleotide arrays useful in the present invention are well known in the art (see, e.g., Fodor et al., 1991 *Science* 251:767–73; Pease et al. 1994 *Proc. Natl. Acad. Sci. USA* 91:5022–26; Chee et al. 1996 *Science* 274:610–4; Lipshutz et al. 1995 *BioTechniques* 19:442–7). The arrays can contain thousands of oligonucleotides (e.g., 20mer oligonucleotides) representing the set of molecular tags in the total starting cell population. The tag for each of the different strains in the culture hybridizes to a known location on the array, thus facilitating identification of the specific strains that, with increasing culture time or drug concentration, exhibited decreasing (or increasing) hybridization signals on the arrays. In this manner, all molecular tags present in the population can be simultaneously identified without the need for cloning or sequencing. Moreover, it is possible to analyze tags from several timepoints taken during the course of the growth study. The amplified tags from each timepoint can be used to calculate the growth rate of their corresponding strains in the pool.

Amplified sequences can be labeled by, for example, incorporation of a labeled nucleotide (e.g., a fluorescent nucleotide such as Cy3-dUTP or Cy5-dUTP, or a radioactive nucleotide). Labeling can be accomplished by adding detectably labeled nucleotides to a standard PCR reaction containing the appropriate common primers. Unincorporated labeled nucleotides are removed (e.g., by size exclusion chromatography) prior to analysis. Alternatively, the amplified tags can be labeled by virtue of a label bound to a common primer used during amplification.

Hybridization of the labeled sequences to the microarray is accomplished according to methods well known in the art. Hybridization is carried out under hybridization conditions that allow for specific hybridization of the amplified tags to their respective complementary sequence located on the array without significant non-specific cross-hybridization. Where the molecular tags are about 20 nucleotides in length, hybridization is preferably carried out in a hybridization mixture of 6× SSPE-T (0.9 M NaCl, 60 mM $NaH_2PO_4$, 6 mM EDTA, and 0.005% Triton X-100) for 20 min at 37° C., followed by 10 washes in 1× SSPE-T at 22° C. Following hybridization, the microarrays can be scanned to detect hybridization of the amplified molecular tags using a custom built scanning laser microscope as described in Shalon et al., (1996) *Genome Res.* 6:639.

Figure 4:
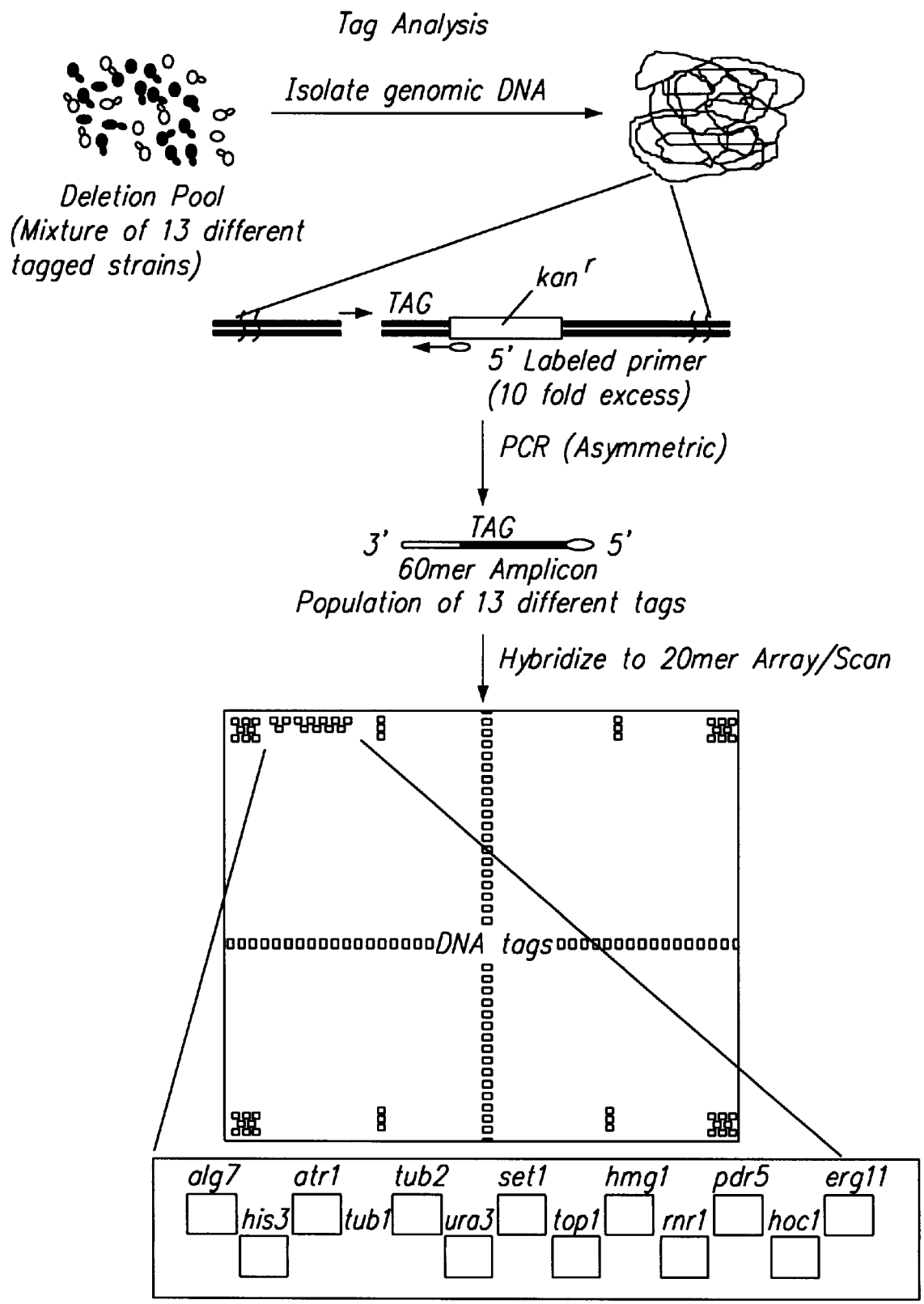
FIG. 4 illustrates an example of analysis of tagged heterozygote deletion strains using an oligonucleotide array.

The relative intensity of the hybridization signals for each tag is determined according to methods well known in the art. The relative hybridization signals can be compared qualitatively (see, e.g., FIG. 12) to, for example, identify heterozygous strains that are depleted from the sample relative to the diploid strain. Where multiple samples of the same set of heterozygous deletion strains is compared, the relative hybridization signals of the deletion and diploid strains can be compared across samples to identify heterozygote strains that become under- or overrepresented with, for example, increasing culture time or increasing drug concentration. Where quantitative results are desired, the relative hybridization signal intensities for each strain can be compared over time with the hybridization signal intensities of a control strain (e.g., wildtype). FIG. 4 provides an example of analysis of tagged heterozygote deletion strains using an oligonucleotide array. The enlarged area of the microarray shows the hybridization of tags of the corresponding heterozygous deletion strain. For example, the square labeled "alg7" is the area of the grid to which the tag corresponding to the alg7Δ/ALG7 strain hybridizes. Areas of hybridization not represented in the enlarged area represent areas of control tag hybridization.

Strains that become underrepresented with increasing culture time (or with increasing drug concentration) relative to a strain expressing the target gene at a higher expression level (e.g. a heterozygote strain that becomes underrepresented relative to a diploid strain) are strains that express a lower level of a target gene that confers a selective advantage under the test growth conditions. For example, where the growth conditions include the presence of a growth-inhibiting drug, the depleted heterozygote contains a deletion in a target sequence encoding a gene product that confers resistance to the drug.

The use of an oligonucleotide array allows for quantitative, sensitive, and simultaneous screening of large numbers of heterozygote strains. For example, tags amplified from a pool containing 6,200 different heterozygotes, at equal abundance, should generate 6,200 hybridization signals of equal intensity on the array. However, depletion of a heterozygous deletion strain (e.g., due to sensitivity to an inhibitory compound) can be detected by a decreased hybridization signal relative to signals of the same strains at earlier timepoints, relative to other heterozygous deletion strains, and relative to the reference strain (e.g., a tagged wildtype strain). Inclusion of at least one molecular tag to identify each individual heterozygous deletion strain and diploid strain within a collection of strains in a culture facilitates screening of drugs in parallel and allows the method of the invention to be automated.

The combination of growth of pooled strains under test conditions and DNA microarrays according to the present invention provides a system of target identification that is potentially genome-wide as well as parallel, highly efficient, and sensitive. By utilizing DNA microarrays and PCR amplification of molecular tags, all strains in the test population can be detected and identified simultaneously, even when individual strains differ greatly in their relative abundance. Moreover, microarrays allow very large numbers of different sequences (e.g., up to about 400,000 different oligonucleotides on a single chip of about 1 sq. in.), thus enabling application of complex probes to whole genome representations for rapid analysis.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is weight average molecular weight, temperature is in degrees centigrade; and pressure is at or near atmospheric.

EXAMPLE 1

Construction of Heterozygous Deletion Strains

Three classes of heterozygous deletion strains of Saccharomyces cerevisiae were produced. Exemplary heterozygous deletion strains were generated using homologous gene transplacement (Rothstein (1991) *Meth. Enzymol.* 194:281) in wildtype diploid strains using standard methods. The resulting heterozygotes carry a deletion in one of the two copies of a given gene. A summary of the strains produced is provided in Table 2.

TABLE 2

Exemplary Heterozygous Deletion Yeast Strains

| Gene | Protein Function | Growth Inhibitor |
| --- | --- | --- |
| Known drugs with known drug targets | | |
| HIS3 | enzyme required for histidine biosynthesis | 3-amino-triazole |
| URA3 | enzyme required for uracil biosynthesis | 5-FOA |
| ALG7 | transferase required for Asn-linked glycosylation (Barnes et al. (1984) Mol Cell. Biol. 4:2381; Rine et al. (1983) Proc. Natl. Acad. Sci. USA 80:6750) | tunicamycin |
| TUB1 | α-tubulin, essential structural mitotic apparatus component | benomyl |
| TUB2 | β-tubulin, essential structural mitotic apparatus component (Shatz et al. (1986)Mol. Cell. Biol. 6:3711) | benomyl |
| TOP1 | topoisomerase I | camptothecin (human anti-cancer drug) |
| HMG1 | HMG-CoA reductase, essential for sterol biosynthesis in yeast and for cholesterol biosynthesis in humans (Basson et al.(1986) Proc. Natl. Acad. Sci. USA 83:5563) | compactin (drug for treating high cholesterol in humans) |
| RNR1 | ribdnuclease reductase, required for nucleotide biosynthesis (Elledge (1990) Genes & Dev. 4:740) | hydroxyurea (human anti-cancer drug) |
| ACT1** | codes for actin | latrunculin B |
| CYH2** | codes for ribosomal protein | cycloheximide |
| Known drugs with unknown drug targets | | |
| ERG11 | important in ergosterol biosynthesis, a cell wall component; detector for, e.g., fluconazole-like antifungal drugs (Kelly et al. (1997) J. Biol. Chem. 272:9986) | fluconazole, nystatin* (antifungal drugs) |
| HOC1 | putative mannosyltransferase; detector for, e.g., calcofluor white-like drugs(Nieman et al. (1997)Genetics 145:637) | calcofluor white (inhibitor of fungal cell wall biosynthesis), hygromycin B*; (anti-fungal drugs) |
| Strains for testing against a mini library of drugs against unknown targets | | |
| SET1 | transcription factor postulated function in chromatin-mediated gene regulation; exhibits mitotic, meiotic, and cell wall phenotypes | Drugs that affect set1Δ/SET1 heterozygotes are unknown |
| Diploid strains | | |
| WT-1 | tagged wild-type strain #1 | not applicable - |
| WT-2 | tagged wild-type strain #2 | not applicable - |

*Haploid deletions are sensitive to these drugs.
**These strains have not yet been constructed.

The three classes of yeast heterozygous deletion strains are designed to 1) test that the method of the invention can be used with known drugs to identify their known drug targets (thus providing proof of the principle upon which the method of the invention is based); 2) test known drugs to identify the drugs' unknown target; and 3) test a mini library of drugs against a set of unknown targets. In each case, the effect of the drug is assayed by comparing the growth rates of the heterozygous deletion strains and wildtype diploid strains in the absence of the drug or in the presence of increasing concentrations of the drug. Growth rate is defined as the cell doubling time in YPD (rich medium) at 30° C.

Heterozygous deletion strains exhibiting increased sensitivity to a drug relative to the reference strain (e.g., a wildtype strain) are identified as carrying deletions in a gene product that is the drug's bona fide target, as being otherwise affected (as judged by a decrease in fitness level) by the gene dosage of the bona fide target, or carrying a gene product that is affected by gene dosage of the bona fide target (e.g., the gene product is downstream in the pathway or weakens a parallel pathway).

EXAMPLE 2

Growth of alg7Δ/ALG7 Heterozygous Deletion Strains (1 copy) and ALG7/ALG7 Wild-type Diploid Strains (2 copy) Under Test Conditions The operability of the method of the invention was first demonstrated by examining whether strains containing either 1 functional copy or 2 functional copies of a known drug resistance gene would exhibit differential growth rates in the in the presence of the drug. To this end, the gene ALG7, which encodes a transferase required for Asn-linked glycosylation, was selected for examination. Gross overexpression of ALG7p is known to confer resistance to drugs such as tunicamycin (Rine et al. 1983 Proc. Natl. Acad. Sci. 50:6750). Thus, yeast cells containing one functional copy of ALG7 are expected to exhibit sensitivity in growth rate in the presence of tunicamycin relative to yeast cells containing two functional copies of ALG7.

Two separate cultures of the alg7Δ/ALG7 heterozygous deletion strain (1 copy) and the wildtype ALG7/ALG7 diploid strain (2 copies) were grown in increasing concentrations of tunicamycin (1) no drug; 2) 0.5 μg/ml tunicamycin; and 3) 2.0 μg/ml tunicamycin). The cultures were grown for a period of 12 hrs, with the optical density ($OD_{600}$) determined at 1 hr intervals. The results are shown in FIG. 5 (no drug), FIG. 6 (0.5 μg/ml tunicamycin), and FIG. 7 (2.0 μg/ml tunicamycin).

Figure 5:
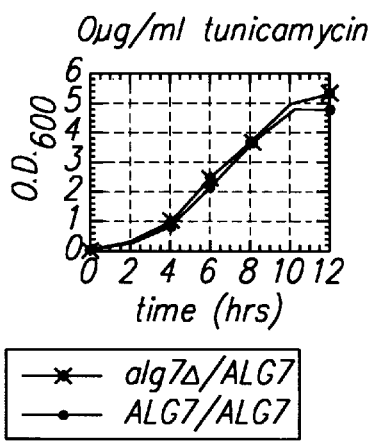
FIG. 5 is a graph showing the growth rates of the heterozygote strain alg7Δ/ALG7 and the wildtype strain ALG7/ALG7 in the absence of tunicamycin.
Figure 6:
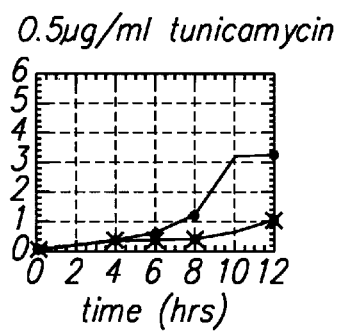
FIG. 6 is a graph showing the growth rates of the heterozygote strain alg7Δ/ALG7 and the wildtype strain ALG7/ALG7 in the presence of 0.5 µg/ml tunicamycin.
Figure 7:
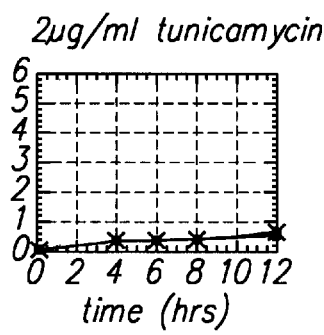
FIG. 7 is a graph showing the growth rates of the heterozygote strain alg7Δ/ALG7 and the wildtype strain ALG7/ALG7 in the presence of 2 µg/ml tunicamycin.

FIG. 5 shows that the alg7Δ/ALG7 heterozygous deletion strain and the ALG7/ALG7 wildtype strain exhibit comparable growth rates in the absence of the drug. Moreover, neither strain grew in the presence of 2.0 μg/ml tunicamycin (FIG. 7). However, at an intermediate concentration of tunicamycin (0.5 μg/ml; FIG. 6), a significant difference in sensitivity between growth rates of the alg7Δ/ALG7 heterozygote and the ALG7/ALG7 wild-type strain was detected. This difference in growth sensitivity was detectable within about 6 to 8 hrs, a relatively short time period, thus largely precluding the appearance of supressors or other secondary mutations within the cell populations.

EXAMPLE 3

Figure 8:
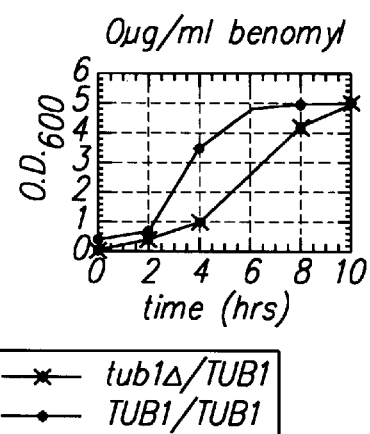
FIG. 8 is a graph showing the growth rates of the heterozygote strain tubΔ1/TUB1 and the wildtype strain TUB1/TUB1 in the absence of benomyl.

Growth of tub1Δ/TUB1 Heterozygous Deletion Strains (1 copy) and TUB1/TUB1 Wild-type Diploid Strains (2 copy) Under Test Conditions The method of the invention was also tested by examining whether strains containing either 1 functional copy or 2 functional copies of TUB1, which encodes α-tubulin protein, a known drug target of the anti-cancer drug benomyl. Two separate cultures of the tub1Δ/TUB1 heterozygous deletion strain (1 copy) and the wildtype TUB1/TUB1 diploid strain (2 copies) were grown in increasing concentrations of benomyl (1) no drug; 2) 25 μg/ml benomyl; and 3) 50 μg/ml benomyl). The cultures were grown for a period of 12 hrs, with the optical density ($OD_{600}$) determined at 1 hr intervals. The results are shown in FIG. 8 (no drug), FIG. 9 (25 μg/ml benomyl), and FIG. 10 (50 μg/ml benomyl).

Figure 9:
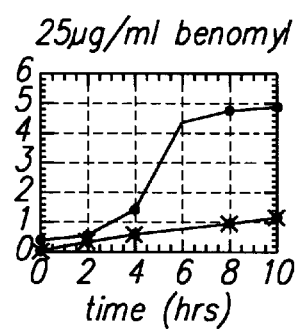
FIG. 9 is a graph showing the growth rates of the heterozygote strain tubΔ1/TUB1 and the wildtype strain TUB1/TUB1 in the presence of 25 µg/ml benomyl.
Figure 10:
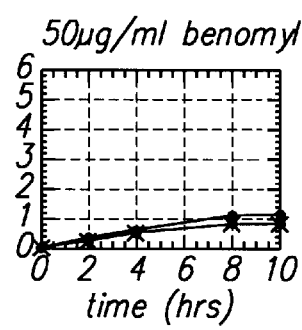
FIG. 10 is a graph showing the growth rates of the heterozygote strain tubΔ1/TUB1 and the wildtype strain TUB1/TUB1 in the presence of 50 µg/ml benomyl.

FIG. 10 shows that at high concentrations of benomyl, both strains were inhibited for growth. However, in the absence of benomyl (FIG. 8), the tub1Δ/TUB1 strain grows slower that the wild-type strain (and is therefore haploinsufficient under these conditions). This observation does not affect our analysis because sensitivity to drugs is relative, and measured as a difference in growth rate. In FIG. 9, for example, it is clear that at 25 μg/ml of benomyl, the difference between the growth rates of the TUB1/TUB1 wild-type strain and the tub1Δ/TUB1 heterozygote strain is significantly larger than the difference in the growth of these strains in the absence of benomyl (FIG. 8).

This example thus demonstrates that the method of the invention is useful in screening candidate bioactive agents for activity against the same target or in the same pathway or cellular process as a known drug. For example, A distinctive feature of our method is that these heterozygote strains can be used to search for new drugs. For example, the tub1Δ/TUB1 strain can serve as a benchmark strain to use to screen for other benomyl-like drugs that inhibit mitosis and might thus represent effective anti-cancer agents. If the tub1Δ/TUB1 strain exhibits an increased sensitivity in the presence of a drug, then this drug is likely to perturb some component of the mitotic apparatus.

EXAMPLE 4

Growth of tub2Δ/TUB2 Heterozygous Deletion Strains (1 copy) and TUB2/TUB2 Wild-type Diploid Strains (2 copy) Under Test Conditions The method of the invention was also tested by examining whether strains containing either 1 functional copy or 2 functional copies of TUB2, which encodes β-tubulin protein, a known drug target of the anti-cancer drug benomyl. Two separate cultures of the tub2Δ/TUB2 heterozygous deletion strain (1 copy) and the wildtype TUB2/TUB2 diploid strain (2 copies) were grown in increasing concentrations of benomyl (1) no drug; 2) 25 μg/ml benomyl; 3) 50 μg/ml benomyl and 4) 100 μg/ml benomyl). (0 mM, 50 mM, 100 mM, and 200 mM). Briefly, overnight culture of each strain grown at 30° C. was diluted to an $OD_{600}$ of 0.05. The diluted strains were allowed to grow one generation to an $OD_{600}$ of 0.1 to refresh the cells. Drug was added at the selected concentrations. The cultures were grown for a period of 10 hrs, with the $OD_{600}$ determined at 1 hr intervals.

While both the tub2Δ/TUB2 and TUB2/TUB2 strains failed to grow to any significant extent in the presence of a high concentration of benomyl, the difference between the growth rates of the TUB2/TUB2 wild-type strain and the tub2Δ/TUB2 heterozygote strain at the intermediate benomyl concentration was significantly larger than the difference in the growth rates of these strains in the absence of benomyl. As with the TUB1 experiments in Example 3, these results thus again verify that differences in benomyl sensitivity is correlated with small incremental differences in copy number of the TUB2 gene.

EXAMPLE 5

Growth of rnr1Δ/RNR1 Heterozygous Deletion Strains (1 copy) and RNR1/RNR1 Wild-type Diploid Strains (2 copy) Under Test Conditions The method of the invention was also tested by examining whether strains containing either 1 functional copy or 2 functional copies of RNR1, which is a detector for hydroxyurea-like drugs (a drug inhibiting DNA replication). Two cultures of the rnr1Δ/RNR1 heterozygous deletion strain (1 copy) and the wildtype RNR1/RNR1 diploid strain (2 copies) were grown in increasing concentrations of hydroxyurea (0 mM, 50 mM, 100 mM, and 200 mM). Briefly, overnight culture of each strain grown at 30° C. was diluted to an $OD_{600}$ of 0.05. The diluted strains were allowed to grow one generation to an $OD_{600}$ of 0.1 to refresh the cells. Drug was added at the selected concentrations. The cultures were grown for a period of 12 hrs, with the $OD_{600}$ determined at 1 hr intervals.

While both the rnr1Δ/RNR1 and RNR1/RNR1 strains failed to grow to any significant extent in the presence of a high concentration of hydroxyurea, the difference between the growth rates of the RNR1/RNR1 wild-type strain and the rnr1Δ/RNR1 heterozygote strain at the intermediate hydroxyurea concentration was significantly larger than the difference in the growth rates of these strains in the absence of drug. These results thus verify that differences in hydroxyurea sensitivity is correlated with small incremental differences in copy number of the RNR1 gene.

EXAMPLE 6

Growth of his3Δ/HIS3 Heterozygous Deletion Strains (1 copy) and HIS3/HIS3 Wild-type Diploid Strains (2 copy) Under Test Conditions The ability to detect growth rate differences between strains carrying 1 copy or 2 copies of a "non-essential" drug target, such as HIS3 (which encodes an enzyme essential for histidine biosynthesis) was tested in the method of the invention. To this end, cultures of the his3Δ/HIS3 heterozygous deletion strain (1 copy) and the wildtype HIS3/HIS3 diploid strain (2 copies) were grown in increasing concentrations of 3-aminotriazole (3-AT; 0 mM, 25 mM, 50 mM, and 100 mM). Briefly, overnight culture of each strain grown at 30° C. was diluted to an $OD_{600}$ of 0.05. The diluted strains were allowed to grow one generation to an $OD_{600}$ of 0.1 to refresh the cells. Drug was added at the selected concentrations. The cultures were grown for a period of 12 hrs, with the $OD_{600}$ determined at 1 hr intervals.

While both the his3Δ/HIS3 and HIS3/HIS3 strains grew at comparable rates in the absence of 3-AT, a significant decrease in the growth rate of the his3Δ/HIS3 strain relative to the growth rate of the HIS3/HIS3 strain became detectable with increasing concentrations of 3-AT. These results thus verify that differences sensitivity to depletion of an essential nutrient as detected by growth rate is correlated with small incremental differences in copy number (1 copy versus 2 copies) of the HIS3 gene.

Summary of Experimental Results with
Heterozygous Deletion Strains

Of the five heterozygote deletion (1 copy) strains tested to date, all five exhibit sensitivity to inhibitory drugs relative to wildtype diploid (2 copy) strains. These results strongly support the principle of the method that differences in phenotype are detectable between strains containing 2 functional copies and 1 functional copy of a target gene product-encoding sequence. The results of the Examples 2–6 are summarized in Table 3.

TABLE 3

Summary of Results with Heterozygous Deletion Strains

| Gene | Growth Inhibited By | Haploinsufficient* |
|---|---|---|
| Known drug targets with known drugs | | |
| HIS3 | 3-amino-triazole | yes |
| URA3 | 5-FOA | not tested |
| ALG7 | tunicamycin | yes |
| TUB1 | benomyl | yes |
| TUB2 | benomyl | yes |
| TOP1 | camptothecin | not tested |
| HMG1 | compactin | not tested |
| RNR1 | hydroxyurea | yes |
| ACT1 | latrunculin B | not tested |
| CYH2 | cycloheximide | not tested |
| Unknown drug targets with known drugs | | |
| ERG11 | | not tested |
| HOC1 | | not tested |
| Strains for testing against a mini library of drugs against unknown targets | | |
| SET1 | | not tested |

*Haploinsufficiency = detectable differential growth between heterozygous deletion strain and (1 copy strain) and diploid strain (2 copy strain)

EXAMPLE 7

Testing Heterozygous Deletion Strains Containing Deletions for Unknown Drug Targets and Having a Known Drug Sensitivity The method of the invention can also be used to analyze heterozygote strains for genes where the haploid deletion is known to be sensitive to particular drugs, but the precise target of the drug is not known. In this case, the deleted gene clearly does not code for the drug target because it is not present in the sensitive haploid strain. The bona fide drug target could be 1) a gene product that is semi-redundant to the deleted gene product, 2) a gene product in the same pathway, or 3) a gene product that improves the fidelity of the pathway in question. These strains are typically sensitive to more than one drug.

For example, the ERG11 and HOC1 genes, important for cell wall biosynthesis, fall into this category. Both ERG11 and HOC1 haploids are sensitive to drugs that target the cell wall. These drugs must target a different gene product that is important to cell wall fidelity, the drug sensitivity only measurable in erg11Δ and hoc1Δ strains. The corresponding heterozygotes erg11Δ/ERG11 and hoc1Δ/HOC1 can be tested in the method of the invention to find a drug that is the direct target of the heterozygote gene product encoded by ERG11 and HOC1, respectively. These heterozygous deletion strains will be more sensitive to drugs that directly target the deleted gene product than to drugs that target other gene products. Thus, sensitivity of the heterozygous deletion strains to drugs that directly target the ERG11 or HOC1 gene products will be greater than the sensitivity of these strains to the drugs to which the haploid deletion is sensitive. The quantitative nature of the method of the invention can facilitate ranking of drugs with respect to their efficacy, thereby allowing reconstruction of complex cellular pathways.

EXAMPLE 8

Screening of Potential Targets of Unknown Function and Screening Multiple Candidate Drugs The method of the invention also allows the testing of many different potential targets of unknown function for the inhibition by drugs. The set1Δ/SET1 heterozygote is an examples of a strain amenable to such analysis. SET1 encodes a relatively uncharacterized transcription factor that is homologous to the oncogene ALL-1. Heterozygous deletion strains in SET1 exhibit mitotic, meiotic and cell wall phenotypes. Because little is known about what drugs might affect the set1Δ/SET1 heterozygotes, this strain in combination with a SET1/SET1 wildtype diploid strain can be analyzed in the present method to identify drugs that elicit differences in growth rate, thereby indicating that the drug inhibits a gene product encoded by SET1 or that is deficient in set1Δ/SET1 heterozygotes. To this end, the set1Δ/SET1 and SET1/SET1 strains can be grown in the presence of a combination of candidate drugs, i.e., a mini library of candidate drugs, where the combination includes drugs affecting diverse cellular processes and pathways. Where an inhibition of growth of the set1Δ/SET1 strain relative to the SET1/SET1 strain is observed in the presence of increasing concentrations of any one mini-library of drugs, the drugs within that mini-library are further analyzed.

EXAMPLE 9

Screening Multiple Potential Drug Targets

Multiple potential drug targets can be screened by pooling a set of heterozygous deletion strains into a single culture. The genes deleted in the collection of heterozygous strains can be representative of a desired class of genes, or can be representative of the entire genome of the host cell. Wildtype diploid cells containing a molecular tag in a non-functional gene serve as the two copy strain. The heterozygous strains and the diploid strain are grown in a single culture in either the presence of the drug or candidate drug (test) or in the absence of drug (control). Samples are taken from the test and control cultures every two hours for up to about 12 hours. DNA from each of the samples is then subjected to PCR using the common primers and detectably-labeled nucleotides. The labeled amplified tags are then hybridized to an array containing each of the molecular tags of the heterozygous strains and of the diploid strain.

The hybridization signals on the array are then analyzed to identify tags that become less intense with time relative to the hybridization signal of the diploid strain tag. If a heterozygote tag's hybridization signal is weaker with increasing culture time of the sample when compared to the diploid tag signal, then the candidate drug is a growth inhibitor and the "disappearing" tag indicates a heterozygote strain containing a deletion in a gene that confers resistance to the drug. The identified heterozygous strain can then be further characterized by repeating the method using varying concentrations of the drug.

EXAMPLE 10

Screening of Multiple Potential Drug Targets to Identify Drug Target of Tunicamycin Fourteen strains, including 13 heterozygous deletion strains (alg7Δ/ALG7, atr1Δ/ATR1, tub2Δ/TUB2, set1Δ/SET1, hmg1Δ/HMG1, pdr5Δ/PDR5, erg11Δ/ERG11, his3Δ/ his3, tub1Δ/TUB1, ura3Δ/URA3, top1Δ/TOP1, mr1Δ/RNR1, and hoc1Δ/HOC1) and a tagged diploid strain (hoΔ/ho) were grown in a single culture. The pool was created by adding an equal number (approximately $2 \times 10^7$) of cells from each of the 14 strains to a culture tube and mixing. The pool was then pelleted and resuspended in a volume such that the final $OD_{600}$ was 1.0. The pool was then diluted to an $OD_{600}$ of 0.05 and allowed to grow for one generation to an $OD_{600}$ of 0.1. The pool was then divided into two cultures, one with no drug and one with 0.5 μg/ml tunicamycin. The cultures were grown and aliquots containing $2 \times 10^7$ cells were harvested at t=0 hrs, 9 hrs, 11 hrs, 22 hrs, and 48 hrs for subsequent analysis on the high-density oligonucleotide array. Aliquots were pelleted and frozen at $-20°$ C. Cultures were diluted 1:50 fold in prewarmed median when they reached an OD of 1.0 in order to ensure that they were in log phase throughout the experiment.

Genomic preps were produced from the aliquots of culture collected from each timepoint during the course of the experiment. The tags were amplified from each aliquot using the common primers, one of which was labeled with 5'-fluorescein. The amplicons were then directly hybridized to the array in a 100 μl reaction containing 6× SSPE-T, 0.5 nM control oligo, and 80 μl of the tag amplification reaction. The hybridization to the chip was for 30 min at 42° C. The array was subsequently washed five times with 6× SSPE-T. The arrays were then scanned with the fluorescent scanner to produce the image shown in FIG. 12. The intensity of each element in the array indicates the abundance of the tag (and thus the strain) in the pool. FIG. 11 provides a correlation of the position of each molecular tag on the array and the identity of the strain with which it is uniquely associated.

Figure 12:
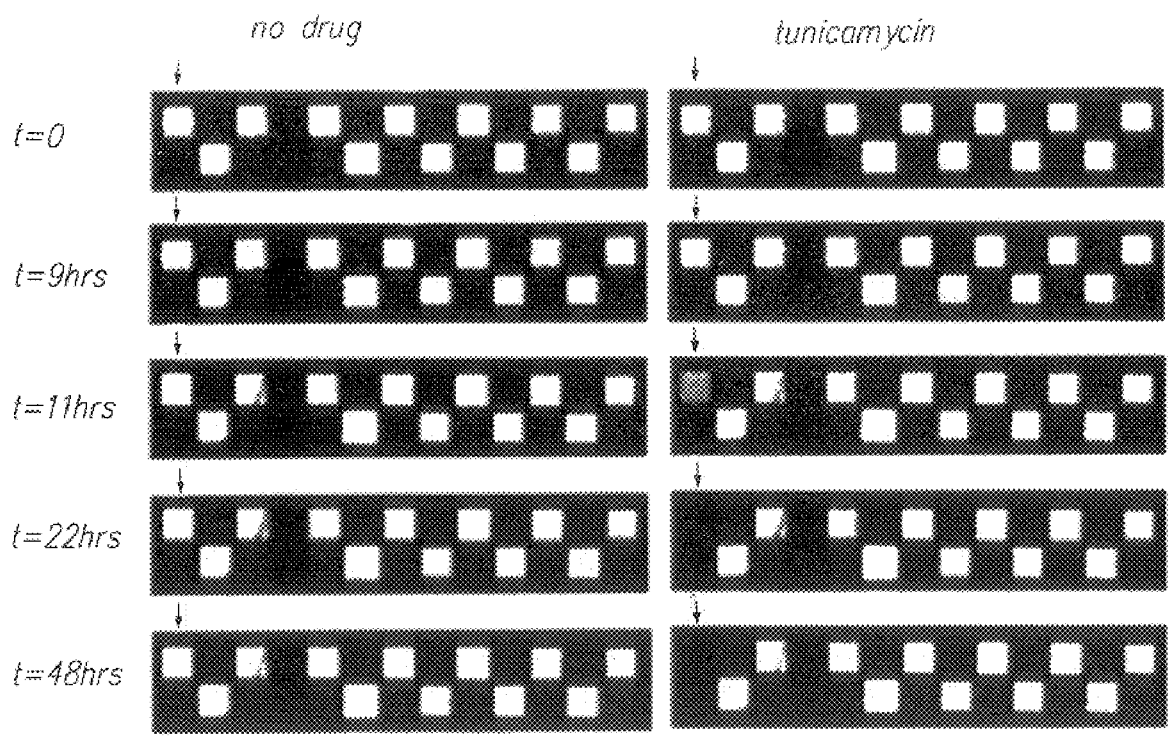
FIG. 12 is a photograph of the oligonucleotide arrays showing the hybridization signals associated with each heterozygous deletion strain in the presence or absence of tunicamycin before drug is added (t=0) and at 9 hrs, 11, hrs, 22 hrs, and 48 hrs of culture.

The results of this example are shown qualitatively in FIG. 12. At t=0 hr and at t=9 hrs of growth of the pool, these was no detectable difference between the hybridization signals of the various molecular tags in either the presence or absence of drug. No hybridization signal was associated with the tub1Δ/TUB1 strain in either the presence or absence of drug. However, it is believed that this is due to an error in the molecular tag sequence, as the strain itself is true to the characteristics of a tub1Δ/TUB1 heterozygous strain. This molecular tag is now being sequenced. Although the data has not been fully analyzed, preliminary results using about 500 strains suggest that the molecular tag errors may occur in less than 5% of all tagged strains and thus should not substantially interfere with analysis. The signal adjacent the erg11Δ/ERG11 signal is due to cross-hybridization to a control tag located elsewhere on the chip. This cross-hybridization did not interfere with analysis.

By 11 hrs, the hybridization signal of the tag associated with the alg7Δ/ALG7 strain was significantly faded in the presence of drug relative to the signal associated with the wildtype strain (not shown), the signals of the other tags in the presence and absence of drug. The signal of the alg7Δ/ALG7 tag decreased in intensity at 22 hrs and was undetectable at 48 hrs of culture in the presence of drug. In contrast, the signal associated with the wildtype tag was approximately equally intense at all timepoints in both the presence and absence of drug (not shown).

Figure 13:
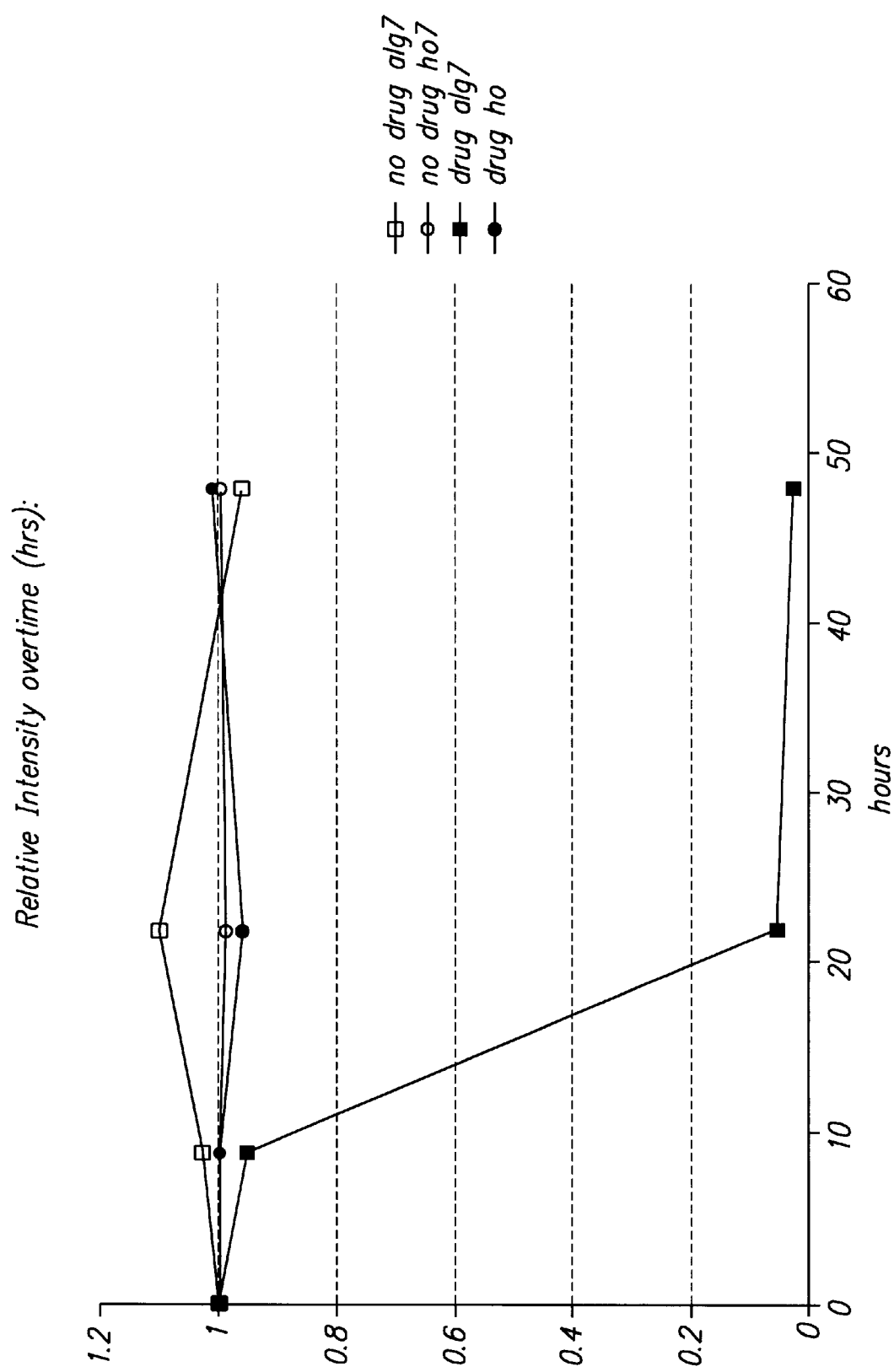
FIG. 13 is a graph showing the relative intensity of the hybridization signals of the molecular tag of the tagged wildtype strain and the molecular tag of the alg7Δ/ALG7 strain, again illustrating the difference in hybridization signal intensities of these strains over time.

FIG. 13 is a graph showing the relative intensity of the hybridization signals of the molecular tag of the tagged wildtype strain and the molecular tag of the alg7Δ/ALG7 strain, again illustrating quantitatively the difference in hybridization signal intensities of these strains over time. In this analysis, the signal intensities for each strain were normalized to 1.0 at t=0. This figure further illustrates that while the growth rate of the alg7Δ/ALG7 strain was comparable to the growth rate of the tagged wildtype strain in the absence of drug, the alg7Δ/ALG7 strain exhibited a markedly decreased growth rate in the presence of drug.

These results show that the method of the invention can be used to accurately identify a drug target in a pool of potential drug targets. In this case, when grown in the presence of tunicamycin, only the strain deficient for expression for the tunicamycin drug target, the alg7Δ/ALG7 strain, exhibited a decreased growth rate in the presence of the drug.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying a nucleotide sequence encoding a target gene product of a bioactive compound, the method comprising the steps of:

culturing a reference host cell and a heterozygous deletion host cell in the presence of a bioactive compound, wherein the heterozygous deletion host cell contains i) a site-specific deletion of a target gene product-encoding sequence, and ii) one functional copy of the target gene product-encoding sequence, and wherein the reference host cell and the heterozygous deletion host cell express the target gene product-encoding sequence at different levels; and comparing growth rates of the reference host cell and the heterozygous deletion host cell;

wherein an alteration in growth rate of the heterozygous deletion host cell relative to the growth rate of the reference host cell indicates that the expression level of the candidate target gene product-encoding sequence is a determinant of resistance or sensitivity to the bioactive compound and the candidate target gene product-encoding sequence encodes a target gene product of the bioactive compound.

2. The method of claim 1, wherein the reference host cell is a wildtype host cell.

3. The method of claim 1, wherein the reference host cell contains a first molecular tag and the heterozygous deletion cell contains a second molecular tag, which second molecular tag is uniquely associated with the site-specific deletion of the heterozygous deletion host cell.

4. The method of claim 1, wherein the reference host cell and the heterozygous deletion host cell are yeast strains.

5. The method of claim 1, wherein the growth rate of the reference host cell is compared to the growth rates of two or more heterozygous deletion host cells, wherein each of the heterozygous deletion host cells contains a deletion in a different target gene product-encoding sequence, and wherein the reference host cell and heterozygous deletion host cells are grown in a single culture.

6. The method of claim 3, wherein said comparing comprises, amplifying the first and second molecular tags, thereby producing first and second amplified tags;

hybridizing the amplified tags to an array of oligonucleotides comprising the first and second molecular tags; and comparing hybridization signals between the first and second molecular tags;

wherein a difference of hybridization signal intensity of the second molecular tag relative to hybridization signal intensity of the first molecular tag is indicative of an alteration in growth rate of the heterozygous deletion host cell in the presence of the bioactive compound.

7. A method for identifying a bioactive compound, the method comprising the steps of:

culturing a reference host cell and a heterozygous deletion host cell in the presence of a candidate bioactive compound, wherein the heterozygous deletion host cell contains i) a site-specific deletion of a target gene product-encoding sequence, and ii) one functional copy of the target gene product-encoding sequence, and wherein the reference host cell and the heterozygous deletion host cell express the target gene product-encoding sequence at different levels; and comparing growth rate of the reference host cell and the heterozygous deletion host cell;

wherein an alteration in growth rate of the heterozygous deletion host cell relative to the growth rate of the reference host cell indicates that the candidate bioactive compound has activity toward the target gene product and that the expression level of the candidate target gene product-encoding sequence is a determinant of resistance or sensitivity to the compound.

8. The method of claim 7, wherein the reference host cell is a wildtype host cell.

9. The method of claim 7, wherein the reference host cell contains a first molecular tag and the heterozygous deletion cell contains a second molecular tag, which second molecular tag is uniquely associated with the site-specific deletion of the heterozygous deletion host cell.

10. The method of claim 7, wherein said comparing comprises, amplifying the first and second molecular tags, thereby producing first and second amplified tags;

hybridizing the amplified tags to an array of oligonucleotides comprising the first and second molecular tags; and comparing hybridization signals between the first and second molecular tags;

wherein a difference in hybridization signal of the second molecular tag relative to hybridization signal of the first molecular tag is indicative of an alteration in growth rate of the heterozygous deletion host cell in the presence of the bioactive compound.

11. The method of claim 7, wherein the reference host cell and the heterozygous deletion host cell are yeast strains.

12. The method of claim 7, wherein the growth rate of the reference host cell is compared to the growth rates of two or more heterozygous deletion host cells, wherein each of the heterozygous deletion host cells contains a deletion in a different target gene product-encoding sequence, and wherein the reference host cell and heterozygous deletion host cells are grown in a single culture.

13. A method for identifying a nucleotide sequence encoding a target gene product of a bioactive compound, the method comprising the steps of:

culturing a first host cell and a second host cell in the presence of a bioactive compound, wherein the first host cell contains a candidate target gene product-encoding sequence expressed at a first expression level and a first molecular tag uniquely associated with the first host cell, and the second host cell contains the candidate target gene product-encoding sequence expressed at a second expression level and a second molecular tag uniquely associated with the second host cell, wherein the second expression level is less than the first expression level; and amplifying the first and second molecular tags, thereby producing first and second amplified tags;

hybridizing the amplified tags to an array of oligonucleotides comprising the first and second molecular tags; and comparing hybridization signals between the first and second molecular tags;

wherein a difference in hybridization signal of the second molecular tag relative to the hybridization signal of the first molecular tag is indicative of a difference in growth rate between the first and second host cells in the presence of the bioactive compound and that the candidate target gene product-encoding sequence encodes a target gene product of the bioactive compound.

14. The method of claim 13, wherein the first and second host cells are grown in a single culture.

15. A method for identifying a bioactive compound, the method comprising the steps of:

culturing a first host cell and a second host cell in the presence of a candidate bioactive compound, wherein the first host cell contains a candidate target gene product-encoding sequence expressed at a first expression level and a first molecular tag uniquely associated with the first host cell, and the second host cell contains the candidate target gene product-encoding sequence expressed at a second expression level and a second molecular tag uniquely associated with the second host cell, wherein the second expression level is less than the first expression level;

amplifying the first and second molecular tags, thereby producing first and second amplified tags;

hybridizing the amplified tags to an array of oligonucleotides comprising the first and second molecular tags; and comparing hybridization signals between the first and second molecular tags;

wherein an alteration in growth rate of the second host cell relative to the growth rate of the first host cell indicates the candidate bioactive compound has activity toward the candidate target gene product.

16. The method of claim 15, wherein the first host cell and the second host cell are grown in a single culture.

* * * * *